United States Patent [19]

Shinohara et al.

[11] Patent Number: 5,756,777
[45] Date of Patent: May 26, 1998

[54] (METH)ACRYLATE HAVING AN ALKENYL GROUP, AN EPOXY (METH)ACRYLATE, A (METH)ACRYLIC RESIN HAVING ALKENYL GROUPS, A (METH)ACRYLIC RESIN HAVING EPOXY GROUPS, A THERMOSETTING RESIN COMPOSITION, A COATING COMPOSITION, A POWDER COATING COMPOSITION

[75] Inventors: Masami Shinohara, Iwakuni; Hideki Matsui, Himehi, both of Japan

[73] Assignee: Daicel Chemical Industries, Ltd., Sakai, Japan

[21] Appl. No.: 541,676

[22] Filed: Oct. 10, 1995

[30] Foreign Application Priority Data

| Oct. 11, 1994 | [JP] | Japan | 6-271677 |
| Oct. 27, 1994 | [JP] | Japan | 6-287300 |
| Nov. 2, 1994 | [JP] | Japan | 6-293926 |
| Jan. 10, 1995 | [JP] | Japan | 7-018487 |
| May 10, 1995 | [JP] | Japan | 7-136172 |
| May 30, 1995 | [JP] | Japan | 7-154054 |

[51] Int. Cl.$^6$ .................... C07D 301/14; C07D 303/12
[52] U.S. Cl. .................... 549/523; 549/557
[58] Field of Search .................... 560/220; 549/523, 549/557

[56] References Cited

U.S. PATENT DOCUMENTS 5,283,360  2/1994  Caubere et al. .................... 56/220

*Primary Examiner*—Joseph L. Schofer
*Assistant Examiner*—Wu C. Cheng
*Attorney, Agent, or Firm*—Morgan & Finnegan, LLP

[57] ABSTRACT

Disclosed are a novel (meth)acrylate having an alkenyl group, a novel epoxy(meth)acrylate, and processes for the preparation thereof.

The (meth)acrylate having an alkenyl group of the present invention can be preferably used as resins for coatings, photo-curable resins, and adhesives by (co)polymerization thereof in the presence or absence of a variety of (meth) acrylic monomers, and the (meth)acrylate compound having an alkenyl group is useful as a silane coupling agent, a starting material for epoxy(meth)acrylates, a modifier for silicone resins, a modifier for unsaturated polyester resins, and a crosslinking agent for acrylic rubbers. The epoxy(meth)acrylate has a well-balanced excellent property between a pot life and reactivity in curing, and it does not contain chlorine, resulting in that a resin therefrom is excellent in an anti-corrosive property and an anti-yellowing property.

Still further, the present invention relates to a (meth)acrylic resin having alkenyl groups as side chains, a (meth)acrylic resin having epoxy groups as side chains, and processes thereof.

In addition, the present invention relates to a thermosetting resin composition, a coating composition and a powder coating composition which have anti-corrosive properties to substrates and anti-yellowing properties in coating layers.

7 Claims, 1 Drawing Sheet

○  3,4-epoxycyclohexylmethyl(meth)acrylate

□  Epoxymethacrylate obtained in Example 9

△  Epoxymethacrylate obtained in Example 10

▽  Epoxymethacrylate obtained in Example 14

◇  Epoxymethacrylate obtained in Example 12

●  Epoxymethacrylate obtained in Example 11

■  β-Methylglycidylmethacrylate

▲  Glycidylmethacrylate

(METH)ACRYLATE HAVING AN ALKENYL GROUP, AN EPOXY (METH)ACRYLATE, A (METH)ACRYLIC RESIN HAVING ALKENYL GROUPS, A (METH)ACRYLIC RESIN HAVING EPOXY GROUPS, A THERMOSETTING RESIN COMPOSITION, A COATING COMPOSITION, A POWDER COATING COMPOSITION

FIELD OF THE INVENTION

The present invention relates to a novel (meth)acrylate having an alkenyl group and to a process for the preparation thereof.

The (meth)acrylate having an alkenyl group of the present invention can be preferably used as resins for coatings, photo-curable resins, and adhesives by (co)polymerization thereof in the presence or absence of a variety of (meth) acrylic monomers, and the (meth)acrylate having an alkenyl group is useful as a silane coupling agent, a starting material for epoxy (meth)acrylates, a modifier for silicone resins, a modifier for unsaturated polyester resins, and a crosslinking agent for acrylic rubbers.

Furthermore, the present invention relates to a novel epoxy(meth)acrylate and to a process for the preparation thereof.

The epoxy(meth)acrylate has a well-balanced excellent property between a pot-life and reactivity in curing, and it does not contain chlorine, resulting in that a resin therefrom is excellent in an anti-corrosive property and anti-yellowing property. That is, the reactivity of the epoxy(meth)acrylate in cationic polymerization with a cationic catalyst is milder than epoxy(meth)acrylates having an alicyclic epoxy group, and quicker epoxy(meth)acrylates having than glycidyl group or beta-methylglycidyl group.

Furthermore, the reactivity of the epoxy(meth)acrylate with compounds having carboxylic group is milder than epoxy(meth)acrylates having glycidyl group, and quicker than epoxy(meth)acrylates having beta-methylglycidyl group.

Still further, the present invention relates to a (meth) acrylic resin having alkenyl groups as side chains, a (meth) acrylic resin having epoxy groups as side chains, and processes thereof.

In addition, the present invention relates to a thermosetting resin composition, and further a coating composition and a powder coating composition which have anticorrosive properties to substrates and anti-yellowing properties in coating layers.

BACKGROUND OF THE INVENTION

An unsaturated carboxylate having a vinyl group is useful as a starting material for oxidation-curable type coating resins, unsaturated polyester resins, photo-curable resins, and silane-coupling agents, and further as a crosslinking agent for acrylic rubbers. In these uses, allylmethacrylates are widely employed at the present time.

However double bond in the allylmethacrylates is unstable, resulting in that there has been a problem of gelling in preparation of polymers of the allylmethacrylates and in radical copolymerization with a variety of acrylic monomers. Furthermore, allyl group is rigid because of few carbon numbers, resulting in that resins obtained therefrom do not have sufficient flexibility. Still further, a reaction velocity in hydrosilylation is slow in the case of preparation of silane coupling agents, and unreacted double bonds often remain in the reaction system.

In the meantime, hitherto, there have been used a variety of resin curing systems in coatings, adhesives, and photo-curable resins.

In the resin systems, there is widely employed a curing system in which there is employed a (meth)acrylic resin having epoxy groups as side chains obtained by (co) polymerization of a (meth)acrylate having epoxy group, owing to exceeding usefulness.

As the (meth)acrylates having epoxy group to be employed in the curing system, there are well known glycidyl methacrylate, beta-methylglycidyl (meth)acrylate, 3,4-epoxycyclohexylmethyl(meth)acrylate. For example, Japanese Patent Publication (Kokai) No. 45577/1990 describes a coating composition in which there is employed a curing reaction between glycidyl methacrylate and compounds having carboxylic groups. Furthermore, Japanese Patent Publication (Kokai) No. 73825/1990 describes a coating composition in which there is employed a cationic curing reaction of an alicyclic epoxy(meth)acrylate such as 3,4-epoxycyclohexylmethyl(meth)acrylate with compounds having silanol groups.

However, as glycidyl methacrylate has an exceedingly high reactivity with the compounds having carboxylic group, in the case when it is employed as a one-liquid type coating composition, a pot-life is short, resulting in causing a problem of gelation. Furthermore, glycidyl group is slow in curing reaction velocity in the case of the use of cationic catalysts.

Accordingly, it is substantially difficult to employ glycidyl methacrylate in the curing system described in the Kokai No. 73825/1990.

Still further, alicyclic epoxy groups in the alicyclic epoxy (meth)acrylate such as 3,4-epoxycyclohexylmethyl(meth) acrylate has a high reactivity in a cationic curing, accordingly, in the case when the alicyclic epoxy(meth) acrylate is employed in a coating system containing compounds having carboxylic groups or in the presence of catalysts having a relatively strong acidity such as phosphoric acid, oxalic acid, p-toluene sulfonic acid, there is a problem that a pot-life is short because a cationic polymerization is caused by hydroxyl groups in the system which act as an initiator, resulting in that there is difficult the selection of curing catalysts exhibiting an appropriate pot-life.

On the other hand, beta-methylglycidyl (meth)acrylate has a mild reactivity with compounds having carboxylic groups or in cationic curing, accordingly, although a pot-life can be lengthened in one-liquid type coatings, there has been a problem that a curing reaction time of period is lengthened or higher curing temperatures require, resulting in that a selection range in curing conditions is narrow.

Furthermore, glycidyl (meth)acrylate and beta-methylglycidyl (meth)acrylate contain chlorine even after purification because these are prepared from epichlorohydrin and beta-methylepichlorohydrin, which are starting materials, respectively, resulting in that it is not able to prevent corrosion in substrates and yellowing in coatings during a curing reaction for baking.

For the purpose of solving the above-mentioned disadvantages, as a result of an intensive investigation, the inventors of this invention have now found that it is possible to solve the various problems by resins in which a (meth) acrylate having an alkenyl group and an epoxy(meth) acrylate are (co)polymerized, respectively.

The (meth)acrylate having an alkenyl group of the present invention can provide a (meth)acrylic resin having alkenyl group-containing side chains by the (co)polymerization in the presence or absence of a variety of polymerizable monomers. The (meth)acrylic resin can be employed as resins for curable reactions in coatings, photo-curable resin, and adhesives, etc. As the (meth)acrylic resin contains double bonds as side chains differently from allylmethacrylate copolymers, it can provide a cured article having excellent flexibility. Furthermore the (meth)acrylic resin optionally contains an inner double bond, it can provide a cured article having an improved crosslinking density.

An epoxy(meth)acrylate of the present invention can provide a (meth)acrylic resin having epoxy group-containing side chains obtained by the (co)polymerization in the presence or absence of a variety of polymerizable monomers. The (meth)acrylic resin has a well-balanced property between a pot-life and reactivity in curing, and has an anti-corrosion property to substrates and anti-yellowing property.

The (meth)acrylic resin having epoxy group-containing side chains of the present invention can provide a thermosetting resin composition which can be employed as a coating composition.

In the case when the thermosetting resin composition of the present invention is employed as a coating composition, it can provide a coating layer having flexibility because epoxy groups which are crosslinking points are situated at a position separated from the main chain of the (meth)acrylic resin.

In the meantime, for more than ten years, powder coating compositions have been widely used in many fields, because, e.g., of the following excellent properties:

(a) it does not contain any solvents, therefore, it has an advantage of presenting less physiological hazards and environmental pollution hazards, and avoiding the risk of fire;

(b) it requires only reasonable costs, because as mentioned above, solvents are not used, and because excess parts of a powder coating composition which is not fixed onto the substrate to be coated at the time of application can be recovered completely;

(c) it has a capability of being used to form thick coating layers of up to 100 microns, which cannot be achieved with paints or varnishes having solvents;

(d) its coated and cured layer does not tend to soften even when exposed to an elevated temperature atmosphere; and (e) it has a characteristic of better adhesion to metal substrates.

An acid-curing type powder coating by use of a polybasic acid or a carboxyl-terminated polyester resin having at least 2 carboxylic groups in a molecule has been widely used because of various kinds of excellent properties, such as ductility of the coating layer, surface hardness of the coating layer, etc., in addition to the above-described (a) to (e).

They can be attained by adjusting the molecular weight and by appropriate selection of a combination of a polycarboxylic acid(s) and a polyhydric alcohol(s), said polyester resin can be readily prepared by an esterification reaction between (n+1) mole of a polycarboxylic acid(s) and n mole of a polyhydric alcohol(s).

A polyester resin having carboxyl groups in terminal positions usually reacts with an epoxy resin to form a cured coating layer as described hereinafter.

Namely, carboxyl groups in terminal positions and epoxy groups react and cure by heating at the presence of catalyst, resulting in formation of tough coating layer.

So-called epi-bis type epoxy resins produced by a reaction between bisphenol A and epichlorohydrin, novolak type epoxy resins produced by a reaction between a novolak phenol resin and epichlorohydrin and the like have been used in the above-described curing reaction with a polyester resin. However, the above-described epoxy resin cannot give sufficient resistance to heat and good outdoor durability to the coated layer made from a corresponding powder coating composition.

Furthermore, a powder coating in which a (meth)acrylic resin having epoxy groups are mixed with a curing agent having carboxylic groups is widely used because of excellent weatherability and gloss.

Hitherto, glycidyl methacrylate has been widely used as the (meth)acrylic resin having epoxy groups. However, the epoxy group in glycidyl methacrylate has an exceedingly high reactivity with the compounds having carboxylic group as described hereinabove.

Accordingly, in the case when a (meth)acrylic resin containing glycidyl methacrylate is kneaded with a curing agent and pigments, etc. to prepare a powder coating composition, there were disadvantages that the powder coating composition is not sufficiently kneaded because of the reaction between epoxy groups and carboxylic groups, and fluidity in melting for baking is insufficient, resulting in that coating layer therefrom does not exhibit an excellent smoothness.

Furthermore, in the case when a carboxyl-terminated polyester resin is employed as the curing agent having carboxylic groups, it is poor in compatibility with the (meth)acrylic resin containing glycidyl methacrylate, resulting in that the smoothness in coating layer therefrom is considerably deteriorated and occasionally pinholes are caused.

In recent years, triglycidyl isocyanurate has been used because a powder coating composition prepared with it can form a layer having excellent resistance to heat, good outdoor durability, and also smoothness on the surface of coating layer.

However, triglycidyl isocyanurate has a human toxicity.

Furthermore, there has increasingly been required highly advantageous properties according to the extension of uses of powder coating compositions in various fields.

The (meth)acrylic resin having epoxy group-containing side chains of the present invention can also provide a powder coating composition having a milder reactivity than epoxy(meth)acrylates having an alicyclic epoxy group, and a faster reactivity than epoxy(meth)acrylates having glycidyl group or beta-methylglycidyl group.

SUMMARY OF THE INVENTION

It is an object of the present invention to provide a (meth)acrylate having an alkenyl group, an epoxy(meth)acrylate, processes for the preparation thereof, a (meth)acrylic resin having alkenyl groups as side chains, a (meth)acrylic resin having epoxy groups as side chains, processes thereof a thermosetting resin composition, a coating composition, and a powder coating composition.

A first aspect of the present invention relates to a (meth)acrylate having an alkenyl group represented by general formula (1-1)

wherein $R^1$ is a hydrogen or a methyl group, $R^a$, $R^b$, and $R^c$ are each independently hydrogen or substituted group represented by general formula (2-1)

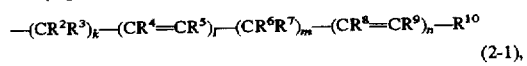

at least one of $R^a$, $R^b$, and R is not hydrogen, $R^2$, $R^6$, $R^7$, and $R^{10}$ are each independently hydrogen or an alkyl group having a carbon number of 1 to 10, $R^3$ is independently hydrogen, or an alkyl, alkenyl or epoxy group having a carbon number of 1 to 10, $R^4$, $R^5$, $R^8$, and $R^9$ are each independently hydrogen or alkyl group having a carbon number of 1 to 5, k is an integer of 0 to 30, l is an integer of 0 to 5, m is an integer of 0 to 30, and n is an integer of 1 to 5.

A second aspect of the present invention relates to a process for the preparation of the (meth)acrylate having an alkenyl group which comprises a condensation reaction accompanied by dehydration between (meth)acrylic acid and alcohols represented by general formula (3-1), or the transesterification of (meth)acrylates with alcohols represented by general formula (3-1)

(3-1)

wherein $R^a$, $R^b$, and $R^c$ are each independently hydrogen or substituted group represented by general formula (3-2)

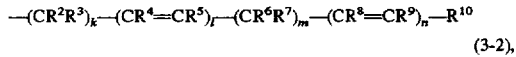

(3-2), at least one of $R^a$, $R^b$, and $R^c$ is not hydrogen, $R^2$, $R^6$, $R^7$, and $R^{10}$ are each independently hydrogen or alkyl group having a carbon number of 1 to 10, $R^3$ is independently hydrogen, or an alkyl, alkenyl or epoxy group having a carbon number of 1 to 10, $R^4$, $R^5$, $R^8$ and $R^9$, are each independently hydrogen or alkyl group having a carbon number of 1 to 5, k is an integer of 0 to 30, l is an integer of 0 to 5, m is an integer of 0 to 30, and n is an integer of 1 to 5.

A third aspect of the present invention relates to an epoxy(meth)acrylate represented by general formula (1-2)

(1-2)

wherein $R^1$ is a hydrogen or a methyl group, $R^{a'}$, $R^{b'}$, and $R^{c'}$ are each an independent hydrogen or substituted group represented by general formula (2-2)

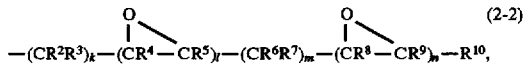

(2-2)

at least one of $R^{a'}$, $R^{b'}$, and $R^{c'}$ is not hydrogen, $R^2$, $R^6$, $R^7$, and $R^{10}$ are each independently hydrogen or alkyl group having a carbon number of 1 to 10, $R^3$ is independently hydrogen, or an alkyl, alkenyl or epoxy group having a carbon number of 1 to 10, $R^4$, $R^5$, $R^8$ and $R^9$ are each independently hydrogen or alkyl group having a carbon number of 1 to 5, k is an integer of 0 to 30, l is an integer of 0 to 5, m is an integer of 0 to 30, and n is an integer of 1 to 5.

A fourth aspect of the present invention relates to a process for the preparation of the epoxy(meth)acrylate.

A fifth aspect of the present invention relates to a (meth)acrylic resin having alkenyl group-containing side chains represented by general formula (1-3)

—COOCR$^a$R$^b$R$^c$    (1-3)

wherein $R^a$, $R^b$, and $R^c$ are each independently hydrogen or substituted group represented by general formula (2-1)

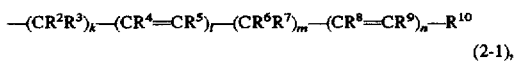

(2-1), at least one of $R^{a'}$, $R^{b'}$, and $R^{c'}$ is not hydrogen, $R^2$, $R^6$, $R^7$, and $R^{10}$ are each independently hydrogen or alkyl group having a carbon number of 1 to 10, $R^3$ is independently hydrogen, or an alkyl, alkenyl or epoxy group having a carbon number of 1 to 10, $R^4$, $R^5$, $R^8$ and $R^9$, are each independently hydrogen or alkyl group having a carbon number of 1 to 5, k is an integer of 0 to 30, l is an integer of 0 to 5, m is an integer of 0 to 30, and n is an integer of 1 to 5.

A sixth aspect of the present invention relates to a process for the preparation of the (meth)acrylic resin having alkenyl group-containing side chains.

A seventh aspect of the present invention relates to a (meth)acrylic resin having epoxy group-containing side chains represented by general formula (1-4), or having the epoxy group-containing side chains represented by the general formula (1-4) and side chains represented by general formula (1-4)'

(1-4)

(1-4)' wherein $R^{a'}$, $R^{b'}$, and $R^{c'}$ are each an independent hydrogen or substituted group represented by general formula (2-2), $R^d$ is a functional group capable of reacting with epoxy group

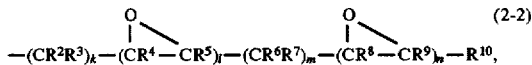

(2-2)

at least one of $R^{a'}$, $R^{b'}$, and $R^{c'}$ is not hydrogen, $R^2$, $R^6$, $R^7$, and $R^{10}$ are each independently hydrogen or alkyl group having a carbon number of 1 to 10, $R^3$ is independently hydrogen, or an alkyl, alkenyl or epoxy group having a carbon number of 1 to 10, $R^4$, $R^5$, $R^8$ and $R^9$, are each independently hydrogen or alkyl group having a carbon number of 1 to 5, k is an integer of 0 to 30, l is an integer of 0 to 5, m is an integer of 0 to 30, and n is an integer of 1 to 5.

A eighth aspect of the present invention relates to a process for the preparation of the (meth)acrylic resin having epoxy group-containing side chains.

A ninth aspect of the present invention relates to a thermosetting resin composition comprising a (meth)acrylic resin having epoxy group-containing side chains represented by general formula (1-4) and side chains represented by general formula (1-4)'

(1-4)

(1-4)' wherein $R^{a'}$, $R^{b'}$, and $R^{c'}$ are each an independent hydrogen or substituted group represented by general formula (2-2), $R^d$ is a functional group capable of reacting with epoxy group

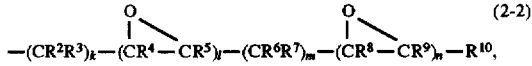

(2-2)

at least one of $R^{a'}$, $R^{b'}$, and $R^{c'}$ is not hydrogen, $R^2$, $R^6$, $R^7$, and $R^{10}$ are each independently hydrogen, alkyl group having a carbon number of 1 to 10, $R^3$ is independently hydrogen, or an alkyl, alkenyl or epoxy group having a carbon number of 1 to 10, $R^4_4$, $R^5$, $R^8$ and $R^9$, are each independently hydrogen or alkyl group having a carbon number of 1 to 5, k is an integer of 0 to 30, l is an integer of 0 to 5, m is an integer of 0 to 30, and n is an integer of 1 to 5 and, optionally a compound having functional groups capable of reacting with an epoxy group.

A tenth aspect of the present invention relates to a coating composition containing the thermosetting resin composition.

A eleventh aspect of the present invention relates to a powder coating composition containing the thermosetting resin composition.

DETAILED DESCRIPTION OF THE INVENTION

Figure 1:
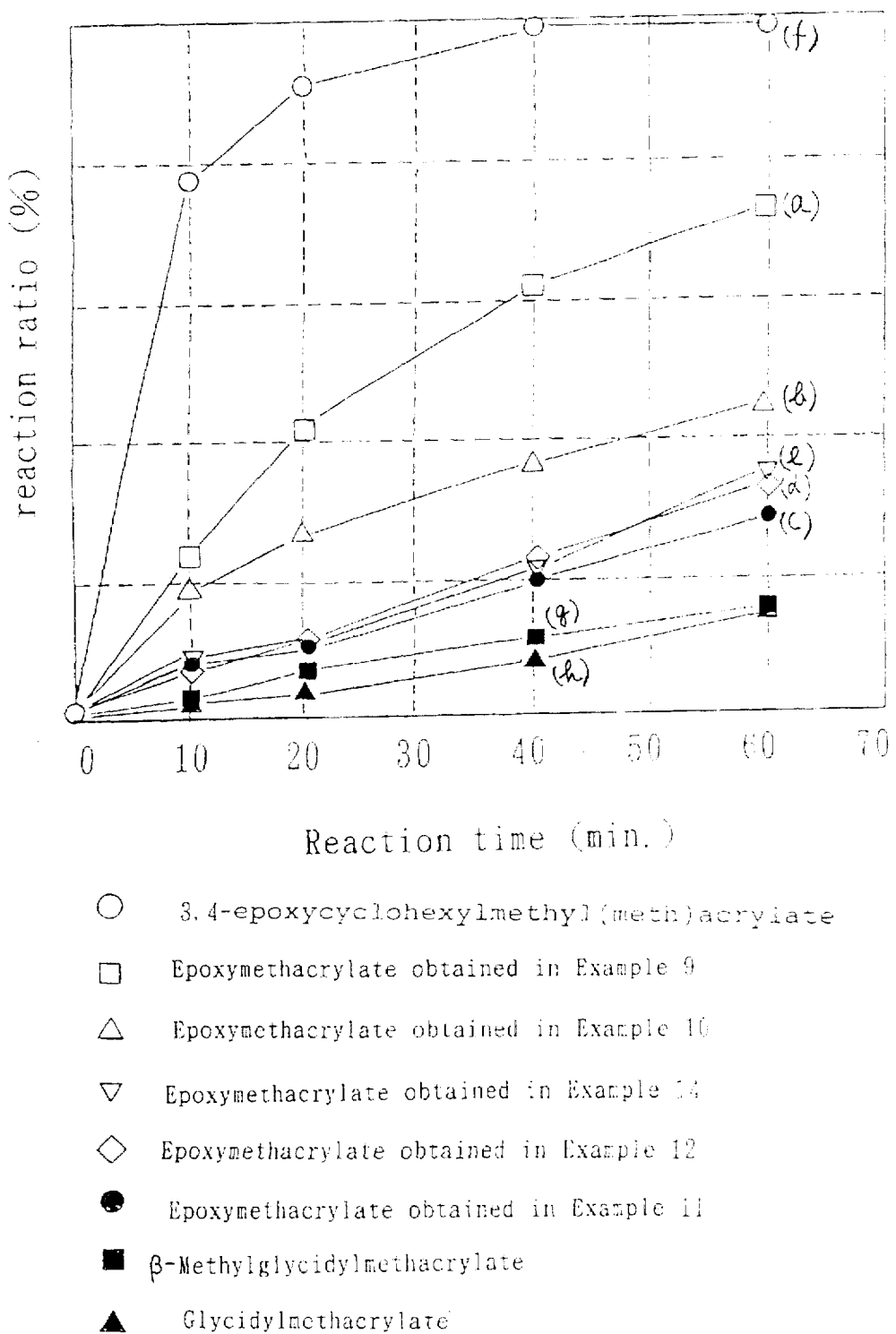
FIG. 1 is a graph exhibiting respective reactivity of the epoxy(meth)acrylates obtained in Examples 9–12 and 14.

The present invention will be described hereinafter in more detail.

According to a first aspect of the present invention, there is provided a (meth)acrylate having an alkenyl group represented by general formula (1-1)

$$CH_2=CR^1-COOCR^aR^bR^c \quad (1-1)$$

wherein $R^1$ is a hydrogen or a methyl group, $R^a$, $R^b$, and $R^c$ are each independently hydrogen or substituted group represented by general formula (2-1)

$$-(CR^2R^3)_k-(CR^4=CR^5)_l-(CR^6R^7)_m-(CR^8=CR^9)_n-R^{10} \quad (2-1),$$

at least one of $R^a$, $R^b$, and $R^c$ is not hydrogen, $R^2$, $R^6$, $R^7$, and $R^{10}$ are each independently hydrogen or alkyl group having a carbon number of 1 to 10, $R^3$ is independently hydrogen, or an alkyl, alkenyl or epoxy group having a carbon number of 1 to 10, $R^4$, $R^5$, $R^8$ and $R^9$, are each independently hydrogen or alkyl group having a carbon number of 1 to 5, k is an integer of 0 to 30, l is an integer of 0 to 5, m is an integer of 0 to 30, and n is an integer of 1 to 5.

According to a second aspect of the present invention, there is provided a process for the preparation of the (meth)acrylate having an alkenyl group which comprises a condensation reaction accompanied by dehydration between (meth)acrylic acid and alcohols represented by general formula (3-1), or the transesterification of (meth)acrylates with alcohols represented by general formula (3-1)

$$HO-CR^aR^bR^c \quad (3-1)$$

wherein $R^a$, $R^b$, and $R^c$ are each independent hydrogen or substituted group represented by general formula (3-2)

$$-(CR^2R^3)_k-(CR^4=CR^5)_l-(CR^6R^7)_m-(CR^8=CR^9)_n-R^{10} \quad (3-2),$$

at least one of $R^a$, $R^b$, and $R^c$ is not hydrogen, $R^2$, $R^6$, $R^7$, and $R^{10}$ are each independently hydrogen or alkyl group having a carbon number of 1 to 10, $R^3$ is independently hydrogen, or an alkyl, alkenyl or epoxy group having a carbon number of 1 to 10, $R^4$, $R^5$, $R^8$ and $R^9$, are each independently hydrogen or alkyl group having a carbon number of 1 to 5, k is an integer of 0 to 30, l is an integer of 0 to 5, m is an integer of 0 to 30, and n is an integer of 1 to 5.

The (meth)acrylate having an alkenyl group represented by the general formula (1-1) of the present invention can be prepared by the condensation reaction accompanied by dehydration between (meth)acrylic acid and alcohols represented by the general formula (3-1), or the transesterification of (meth)acrylates with alcohols represented by the general formula (3-1).

The alcohols represented by the general formula (3-1) essentially contain at least one unsaturated double bonds in the molecule.

In the general formula (1-1), $R^1$ is a hydrogen or a methyl group, which depends upon the selection of acrylic acid (or acrylates) or methacrylic acid (or methacrylates) as a starting material. Structural unit represented by the general formula (2-1) corresponds to a residual group of the alcohols represented by the general formula (3-1).

In the general formula (3-1), $R^2$, $R^4$, $R^5$, $R^6$, $R^7$, $R^8$, $R^9$, and $R^{10}$ are each independently hydrogen or alkyl group having a carbon number of 1 to 10, and preferably hydrogen or an alkyl group having a carbon number of 1 to 3, particularly, methyl group or vinyl group, $R^3$ is independently hydrogen, or an alkyl, alkenyl or epoxy group having a carbon number of 1 to 10. In the general formula (3-1), k is an integer of 0 to 30, preferably 0 to 10, l is an integer of 0 to 5, preferably 0 to 2, m is an integer of 0 to 30, preferably 0 to 10, and n is an integer of 1 to 5, preferably 1 to 2, particularly, k+m is preferably not more than 5.

In the case when k or m exceeds 30, crosslinking density in a cured article cannot be increased because of excessively long methylene chains, unpreferably resulting in that mechanical strength becomes poor. Furthermore, in the case when l or n exceeds 5, crosslinking density in a cured article is partially increased excessively, unpreferably resulting in that the cured article becomes rigid and brittle.

As specific examples of the alcohols represented by the general formula (3-1), there is exemplified a compound such as, for example, 3-methyl-2-butene-1-ol, 3-methyl-3-butene-1-ol, 2,7-octadienol, 7-octene-1-ol, and 1,7-octadiene-3-ol, etc.

As specific examples of the (meth)acrylate represented by the general formula (1-1) of the present invention, there are exemplified $$CH_2=CR^1-COO(CH_2)_6-CH=CH_2 \quad (4-1)$$

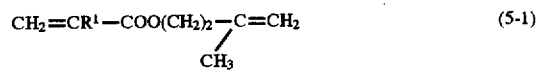
(5-1)

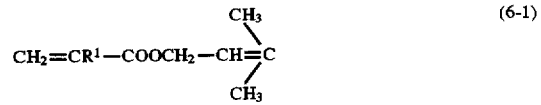
(6-1)

$$CH_2=CR^1-COOCH_2-CH=CH-(CH_2)_3-CH=CH_2 \quad (7-1)$$

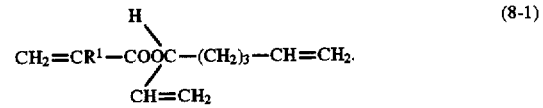
(8-1)

In the general formulae (4-1) to (8-1), $R^1$ is a hydrogen or a methyl group, which depends upon the selection of acrylic acid (or acrylates) or methacrylic acid (or methacrylates) as a starting material.

As specific examples of the (meth)acrylates to be employed as a starting material as well as (meth)acrylic acid, there are exemplified methyl(meth)acrylate, ethyl(meth)acrylate, propyl(meth)acrylate, and butyl(meth)acrylate.

(meth)acrylic acid or (meth)acrylates are employed in an amount of 0.1 to 10.0 mol, preferably 1.0 to 3.0 mol based on 1 mol of the alcohols from a viewpoint of reaction velocity and economy.

In the case when it is below 0.1, although (meth)acrylic acid or (meth)acrylates are effectively converted to a desired product, it unpreferably requires a large amount of energy for the recovery of the alcohols. On the contrary, in the case when it exceeds 10, although it is preferred from a viewpoint of the selectivity and conversion ratio of alcohols, (meth) acrylic acid or (meth)acrylates is not effectively converted to a desired product, it unpreferably requires a large amount of energy for the recovery of unreacted (meth)acrylic acid or (meth)acrylates.

The condensation reaction accompanied by dehydration or the transesterification in the present invention is preferably carried out in the presence of catalysts.

The catalysts to be employed include known catalysts for the conventional condensation reaction accompanied by dehydration or the transesterification.

Specifically, there can be employed organic sulfonic acids such as p-toluene sulfonic acid, metasulfonic acid, and fluorosulfuric acid, inorganic acids such as sulfuric acid, phosphoric acid, and perchloric acid, bases such as sodium alcoholates, lithium hydroxide, aluminum alcoholates, and sodium hydroxide, etc., tin compounds such as stannous octylate, dibutyltin dilaurate, monobutyltin oxide, and stannous chloride, etc., titanium compounds such as tetrabutyl titanate, tetraethyl titanate, and tetraisopropyl titanate, etc.

Of those, there are preferably employed organic sulfonic acids such as p-toluene sulfonic acid from a viewpoint of reaction velocity.

The catalysts are employed in an amount ranging from 1 ppm to 10%, preferably from 5 ppm to 1.0% based on the total amount of starting materials.

In the case when it is below 1 ppm, the reaction velocity becomes unpreferably slow and a yield becomes also low. On the contrary, in the case when it exceeds 10%, a product unpreferably colors and gelation is unpreferably caused by side reactions.

Although the reaction may be carried out even in the absence of solvents, there may be preferably employed a solvent for azeotropically removing water or alcohols which are generated with the progress of the condensation reaction accompanied by dehydration or the transesterification, resulting in effectively accelerating the reaction.

As the solvents, there can be employed benzene, toluene, xylene, n-hexane, n-heptane, and methylisobutyl ketone, etc.

The azeotropic solvents are employed in an amount ranging from 0.1 to 10-fold, preferably from 2 to 5-fold based on the amount of the reactants. The azeotropic solvents distilled off with water or alcohols can be circularly employed after separation.

The reaction can be carried out at temperatures ranging from 65° to 150° C., preferably from 75° to 120° C. from a viewpoint of reducing the reaction period of time and preventing polymerization.

In the case when it is below 65° C., the reaction velocity is excessively slow, resulting in low yield. On the contrary, in the case when it exceeds 150°C., (meth)acrylic acid, (meth)acrylates, and the resulting (meth)acrylates having alkenyl group unpreferably thermally polymerize.

The reaction can be preferably carried out in the presence of polymerization inhibitors as well as streaming air in order to prevent the thermal polymerization of (meth)acrylic acid, (meth)acrylates, and the resulting (meth)acrylates having alkenyl group unpreferably thermally polymerize.

As the polymerization inhibitors, there can be employed hydroquinone, hydroquinone monomethylether, p-methoxyphenol, 2,4-dimethyl-6-t-butylphenol, 3-hydroxythiophenol, alpha-nitroso-beta-naphtol, p-benzoquinone, 2,5-dihydroxy-p-quinone, and copper salts, etc.

Of those, there can be preferably employed hydroquinone and p-methoxyphenol from a viewpoint of stability.

The polymerization inhibitors are employed in an amount of 0.001 to 5.0%, preferably 0.01 to 1.0% based on the amount of (meth)acrylic acid or (meth)acrylates which are starting materials. In the case when it is below 0.001%, effectiveness as the polymerization inhibitors is minor. On the contrary, even in the case when it exceeds 5%, the effectiveness does not increase, resulting in only becoming uneconomical.

The reaction is preferably carried out in ordinary pressures or slightly reduced pressure conditions.

A reaction crude solution obtained in the condensation reaction or transesterification contains unreacted (meth) acrylic acid or (meth)acrylates. Accordingly, the solution is preferably washed with water, or low-boiling-point ingredients are preferably removed after neutralization with an aqueous alkali solution. There may be employed aqueous alkali solution containing NaOH, KOH, $K_2CO_3$, $Na_2CO_3$, $NaHCO_3$, $KHCO_3$, and $NH_3$, etc.

The aqueous alkali solution can be employed in a wide range of the concentration. Water washing is preferably carried out after neutralization in order to prevent residue of neutralized salts in a product. The removal of the low boiling point ingredients is preferably carried out with a thin-layer evaporator, etc. after neutralization and water washing.

According to a third aspect of the present invention, there is provided an epoxy(meth)acrylate represented by general formula (1-2)

     (1-2)

wherein $R^1$ is a hydrogen or a methyl group, $R^{a'}$, $R^{b'}$, and $R^{c'}$ are each an independent hydrogen or substituted group represented by general formula (2-2)

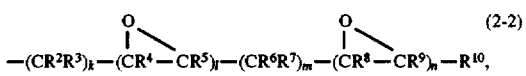     (2-2)

at least one of $R^{a'}$, $R^{b'}$, and $R^{c'}$ is not hydrogen, $R^2$, $R^6$, $R^7$, and $R^{10}$ are each independently hydrogen or alkyl group having a carbon number of 1 to 10, $R^3$ is independently hydrogen, or an alkyl, alkenyl or epoxy group having a carbon number of 1 to 10, $R^4$, $R^5$, $R^8$ and $R^9$ are each independently hydrogen or alkyl group having a carbon number of 1 to 5, k is an integer of 0 to 30, l is an integer of 0 to 5, m is an integer of 0 to 30, and n is an integer of 1 to 5.

According to a fourth aspect of the present invention, there is provided a process for the preparation of the epoxy(meth)acrylate.

The epoxy(meth)acrylate represented by the general formula (1-2) are prepared by the epoxidation of the (meth) acrylate represented by general formula (1-1) of the first aspect described hereinabove with an epoxidation agent.

Accordingly, in the formula (1-2), $R^1$, $R^2$, $R^3$, $R^4$, $R^5$, $R^6$, $R^7$, $R^8$, $R^9$, $R^{10}$, k, l, m, and n are all the same as in the formula (1-1).

As the epoxidation agent to be employed, there are exemplified organic peracids such as performic acid, peracetic acid, perpropionic acid, m-chloroperbenzoic acid, trifluoroperacetic acid, perbenzoic acid, etc., hydroperoxides such as t-butylhydroperoxide, cumylhydroperoxide, tetrallyl-hydroperoxide, diisopropylbenzenehydroperoxide, and hydrogen peroxide, etc.

The epoxidation agent is employed in a ratio of from 0.1 to 10 mol, preferably from 0.5 to 2 mol, more preferably from 0.8 to 1.2 mol based on 1 mol of alkenyl group in the (meth)acrylate represented by general formula (1-1).

In the case when the ratio exceeds 10, the (meth)acrylate represented by general formula (1-1) is preferably converted to the epoxy(meth)acrylate, and the reaction period can be preferably shortened, resulting in reduction of the loss of the (meth)acrylate by the polymerization.

However, side reactions occur by excessive amounts of the epoxidation agent and the selectivity of the epoxidation agent lowers, and further it unpreferably requires large amounts of costs for recovery of the unreacted epoxidation agent. On the contrary, in the case when the ratio is below 0.1, although the epoxidation agent is selectively converted and side reactions are preferably prevented, the (meth) acrylate unpreferably polymerize, resulting in increasing the loss of the (meth)acrylate, and further it unpreferably requires large amounts of costs for recovery of the unreacted (meth)acrylate.

The epoxidation reaction is carried out in a temperature range of 0° to 150° C., more specifically, less than the maximum temperature in which epoxidation reaction more predominantly causes than decomposition reaction of the epoxidation agents. For example, in the case when peracetic acid is employed, it is less than 70° C., and in the case when t-butylhydroperoxide is employed, it is less than 150° C. When the reaction temperature is low, there requires a long time of period for completion of the reaction.

In the case of peracetic acid, the minimum temperature is preferably 0° C., and in the case of t-butylhydroperoxide, the minimum temperature is preferably 20° C.

Although the reaction may be carried out even in the absence of solvents, there may be preferably employed solvents such as benzene, toluene, and xylene, etc. which are aromatic solvents, chloroform, dimethylchloride, carbon tetrachloride, and chlorobenzene, etc. which are halogenated solvents, ethyl acetate and butylacetate, etc. which are ester compounds, acetone and methylisobutyl ketone, etc. which are ketone compounds, 1,2-dimethoxy ethane, etc. which is an ether compound.

The epoxidation reaction can be preferably carried out in the presence of polymerization inhibitors in order to prevent the thermally radical polymerization of the starting (meth) acrylates.

As the polymerization inhibitors, there are employed hydroquinone, hydroquinone monomethylether, p-methoxyphenol, 2,4-dimethyl-6-t-butylphenol, 3-hydroxythiophenol, alpha-nitroso-beta-naphtol, p-benzoquinone, 2,5-dihydroxy-p-quinone, and copper salts, etc. Of those, there are preferably employed hydroquinone and p-methoxyphenol from a viewpoint of stability.

The polymerization inhibitors are employed in an amount of 0.001 to 5.0%, preferably 0.01 to 1.0% based on the amount of starting (meth)acrylates. In the case when it is below 0.001%, effectiveness as the polymerization inhibitors is minor. On the contrary, even in the case when it exceeds 5%, effectiveness does not increase, resulting in becoming uneconomical. The polymerization inhibitors are preferably dissolved in the starting (meth)acrylates before the epoxidation reaction.

Furthermore, the epoxidation reaction can be preferably carried out in the presence of air in order to prevent the thermally radical polymerization of the starting (meth) acrylates.

A reaction crude solution obtained in the epoxidation reaction is preferably washed with water or low boiling point ingredients are preferably removed after neutralization with an aqueous alkali solution.

There may be employed aqueous alkali solution containing NaOH, KOH, $K_2CO_3$, $Na_2CO_3$, $NaHCO_3$, $KHCO_3$, and $NH_3$, etc.

The aqueous alkali solution can be employed in a wide range of the concentration. Water washing is preferably carried out after neutralization in order to prevent residue of neutralized salts in a product. The removal of the low-boiling-point ingredients is preferably carried out with a thin layer evaporator, etc. after neutralization and water washing.

According to a fifth aspect of the present invention, there is provided a (meth)acrylic resin having alkenyl group-containing side chains represented by general formula (1-3)

—COOCR$^a$R$^b$R$^c$ (1-3)

wherein R$^a$, R$^b$, and R$^c$ are each independently hydrogen or substituted group represented by general formula (2-1)

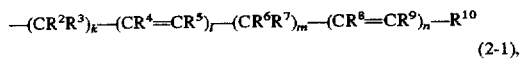

—(CR$^2$R$^3$)$_k$—(CR$^4$=CR$^5$)$_l$—(CR$^6$R$^7$)$_m$—(CR$^8$=CR$^9$)$_n$—R$^{10}$ (2-1), at least one of R$^a$, R$^b$, and R$^c$ is not hydrogen, R$^2$, R$^6$, R$^7$, and R$^{10}$ are each independently hydrogen or alkyl group having a carbon number of 1 to 10, R$^3$ is independently hydrogen, or an alkyl, alkenyl or epoxy group having a carbon number of 1 to 10, R$^4$, R$^5$, R$^8$ and R$^9$, are each independently hydrogen or alkyl group having a carbon number of 1 to 5, k is an integer of 0 to 30, l is an integer of 0 to 5, m is an integer of 0 to 30, and n is an integer of 1 to 5.

According to a sixth aspect of the present invention, there is provided a process for the preparation of the (meth)acrylic resin having alkenyl group-containing side chains represented by general formula (1-3) comprising the radical (co)polymerization of the (meth)acrylate having alkenyl group represented by general formula (1-1) in the presence or absence of a monomer having an unsaturated double bond.

The (meth)acrylic resin having alkenyl group-containing side chains represented by general formula (1-3) of the present invention can be prepared by the radical (co) polymerization of the (meth)acrylate having alkenyl group represented by general formula (1-1) in the presence or absence of a polymerizable monomer having an unsaturated double bond.

As the polymerizable monomer having an unsaturated double bond, there can be employed a variety of monomers which are employed in processes for the preparation of the conventional (meth)acrylic resins, which specifically include vinyl monomers such as styrene, 2-methyl styrene, vinyl acetate, and vinyl chloride, etc., (meth)acrylic acid, (meth)acrylates such as methyl(meth)acrylate, propyl(meth) acrylate, butyl(meth)acrylate, pentyl(meth)acrylate, and hexyl(meth)acrylate, (meth)acrylates having hydroxylic group such as 2-hydroxyethyl(meth)acrylate, 2-hydroxypropyl(meth)acrylate, 2-hydroxybutyl(meth) acrylate, a lactone-modified 2-hydroxyethyl(meth)acrylate, etc. Furthermore, there can be also employed (meth) acrylates such as methoxy diethyleneglycol(meth)acrylate, ethoxydiethyleneglycol(meth)acrylate, isooctyloxydiethyleneglycol(meth)acrylate, phenoxytriethyleneglycol(meth)acrylate, methoxytriethyleneglycol(meth)acrylate, methoxypolyethyleneglycol(meth)acrylate, (meth)acrylates having a terminated silane or silyl group such as 2-trimethylsiloxane ethyl(meth)acrylate, (meth)acrylates having a terminated epoxy group such as glycidyl(meth) acrylate and 3,4-epoxycyclohexylmethyl(meth)acrylate, unsaturateddicarboxylic acids such as maleic anhydride and derivatives thereof, etc.

At least one of the monomers may be employed.

The (meth)acrylic resin having alkenyl group-containing side chains represented by the general formula (1-3) of the present invention can be given a variety of properties by the wide selection of the above-described polymerizable monomers.

For example, in the case when (meth)acrylic acid is copolymerized with the (meth)acrylate having alkenyl group represented by the general formula (1-1), a resulting (meth) acrylic resin has double bonds and carboxylic groups as side chains, which can be employed as a resin for alkali-developing type photo-resists.

Furthermore, the (meth)acrylic resin having alkenyl group-containing side chains of the present invention can be employed as a thermosetting resin by hydrosilylation reaction because of the double bonds in the side chains.

In the case when the (meth)acrylate having alkenyl group represented by the general formula (1-1) is copolymerized with the above-described polymerizable monomers, there is preferably selected a mixing ratio in which the concentration of double bonds at side chains in the (meth)acrylic resin having alkenyl group-containing side chains represented by general formula (1-3) ranges from 0.5 to 7.0 mol/kg, and preferably from 1.3 to 3.4 mol/kg.

In the case when it exceeds 7.0 mol/kg, gelation is readily caused in the copolymerization. On the contrary, in the case when it is below 0.5 mol/kg, although the copolymerization readily proceeds, there are not included large amounts of ethylenic double bonds in the (meth)acrylic resin obtained which are necessary for forming crosslinking structures by photo or thermal energy, resulting in that industrial worth of the resin considerably decreases.

It is to be noted that also in the case when the (meth) acrylate having alkenyl group represented by the general formula (1-1) alone is polymerized, there is preferably selected the concentration of double bonds at side chains which ranges from 0.5 to 7.0 mol/kg, and preferably from 1.3 to 3.4 mol/kg by the selection or combination of the alcohols represented by general formula (3-1).

The radical (co)polymerization of the (meth)acrylate having alkenyl group is carried out by conventional methods such as, for example, emulsion polymerization, suspension polymerization, solution polymerization, and bulk polymerization. Of those, solution polymerization in which solvents are employed is preferably carried out from a viewpoint of preventing gelation and capability of homogeneous reaction.

In the case of solution polymerization, solvents are employed in an amount ranging from 0 to 95% by weight, preferably from 60 to 90% by weight based on the total amounts of the monomers.

In the case when it exceeds 95% by weight, although the polymerization is readily carried out, it becomes disadvantageous from a viewpoint of factors concerning productivity such as recovery of the solvents and a plant scale.

The radical (co)polymerization of the (meth)acrylate having alkenyl group in the present invention is carried out in a temperature range of approximately from 30° to 120° C., preferably from 50° to 100° C., which is a temperature range for carrying out conventional radical (co)polymerization.

As the solvents, there may be preferably employed one or more of solvents such as benzene, toluene, and xylene, etc. which are aromatic solvents, methanol, ethanol, and 2-propanol which are alcohols, acetone, methylethyl ketone, and methylisobutyl ketone, etc. which are ketone compounds, diethylether, dibutyl ether, dioxane, etc. which are ether compounds, ethyl acetate, isobutyl acetate, ethyleneglycol monoacetate, and propyleneglycol monoalkyl acetate, etc. which are ester compounds, dimethylformamide and dimethylacetoamide which are amides, chloroform, dimethylchloride, carbon tetrachloride, and chlorobenzene, etc. which are halogenated solvents, etc.

The radical (co)polymerization of the (meth)acrylate having alkenyl group in the present invention is carried out in the presence of one or more of conventional polymerization initiators such as 2,2'-azobisisobutylnitrile and 2,2'-azobis (2,4-dimethylvaleronitrile) which are azobis-based initiators, lauroyl peroxide, di-t-butylperoxide, bis(4-t-butylcyclohexyl)peroxydicarbonate, t-butylperoxy(2-ethylhexanoate), methylethylketone peroxide, and benzoyl peroxide, etc. which are peroxides.

According to a seventh aspect of the present invention, there is provided a (meth)acrylic resin having epoxy group-containing side chains represented by general formula (1-4), or having the epoxy group-containing side chains represented by general formula (1-4) and side chains represented by general formula (1-4)'

  (1-4)

  (1-4)' wherein $R^{a'}$, $R^{b'}$, and $R^{c'}$ are each an independent hydrogen or substituted group represented by general formula (2-2), $R^d$ is a functional group capable of reacting with epoxy group

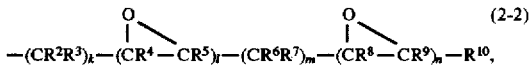  (2-2)

at least one of $R^{a'}$, $R^{b'}$, and $R^{c'}$ is not hydrogen, $R^2$, $R^6$, $R^7$, and $R^{10}$ are each independently hydrogen or alkyl group having a carbon number of 1 to 10, $R^3$ is independently hydrogen, or an alkyl, alkenyl or epoxy group having a carbon number of 1 to 10, $R^4$, $R^5$, $R^8$ and $R^9$, are each independently hydrogen or alkyl group having a carbon number of 1 to 5, k is an integer of 0 to 30, l is an integer of 0 to 5, m is an integer of 0 to 30, and n is an integer of 1 to 5.

According to an eighth aspect of the present invention, there is provided a process for the preparation of the (meth)acrylic resin having epoxy group-containing side chains comprising the radical (co)polymerization of the epoxy(meth)acrylate represented by the general formula (1-2) in the presence or absence of a monomer having an unsaturated double bond.

As the monomer having an unsaturated double bond, there are employed a variety of monomers which are employed in processes of the conventional (meth)acrylic resins, which specifically include vinyl monomers such as styrene, 2-methyl styrene, vinyl acetate, and vinyl chloride, vinylidene chloride, vinyl fluoride, vinylidene fluoride, butadiene, isoprene, etc., monomers having carboxylic group such as (meth)acrylic acid, crotonic acid, itaconic acid, maleic acid, fumaric acid, (meth)acrylates such as methyl(meth)acrylate, propyl(meth)acrylate, butyl(meth) acrylate, pentyl(meth)acrylate, and hexyl(meth)acrylate, (meth)acrylates having hydroxylic group such as 2-hydroxyethyl(meth)acrylate, 2-hydroxypropyl(meth) acrylate, 2-hydroxybutyl(meth)acrylate, a lactone-modified 2-hydroxyethyl(meth)acrylate (for example, PCL-FA and PCL-FM, etc., manufactured by Daicel Chemical Industries, Ltd.), etc., monomers having hydroxylic group such as allyl alcohol and mathallyl alcohol, etc., monomers having amino group such as dimethylaminoethyl(meth)acrylate, monomers having amide group such as (meth)acrylic amide, monomers having nitrile group such as (meth)acrylonitrile, (meth)acrylates such as methoxy diethyleneglycol (meth) acrylate, ethoxydiethyleneglycol (meth)acrylate, isooctyloxydiethyleneglycol (meth)acrylate, phenoxytriethyleneglycol (meth)acrylate, methoxytriethyleneglycol (meth) acrylate, methoxypolyethyl-eneglycol (meth)acrylate, (meth)acrylates having a terminated silane or silyl group such as 2-trimethylsiloxane ethyl (meth)acrylate, (meth) acrylates having a terminated epoxy group such as glycidyl methacrylate and 3,4-epoxycyclohexyl-methyl (meth) acrylate, unsaturated dicarboxylic acids such as maleic anhydride and derivatives thereof, etc. At least one of the monomers may be employed.

The radical (co)polymerization of the epoxy(meth) acrylate represented by the general formula (1-2) in the present invention is preferably carried out in the presence of one or more of conventional polymerization initiators such as 2,2'-azobisisobutylnitrile and 2,2'-azobis (2,4-dimethylvaleronitrile) which are organic azobis-based initiators, lauroyl peroxide, cumen hydroperoxide, and di-t-butylperoxide, methylethylketone peroxide, and benzoyl peroxide, etc. which are peroxides, bis(4-t-butyl-cyclohexyl)peroxydicarbonate, and t-butylperoxy(2-ethylhexanoate), potassium persulfate, ammonium persulfate, sodium persulfate, hydrogen peroxide, which are inorganic water-soluble radical initiators, and redox-initiators.

Furthermore, there can be also employed chain transfer agents in the radical (co)polymerization of the epoxy(meth) acrylate represented by the general formula (1-2) in the present invention.

As the chain transfer agents, there are specifically exemplified mercaptans such as ethylmercaptan and methylmercaptan, alpha-methylstyrene dimer, halogenated hydrocarbons such as carbon tetrachloride and carbon tetrabromide.

The radical (co)polymerization of the epoxy(meth) acrylate is carried out by conventional methods such as, for example, emulsion polymerization, suspension polymerization, solution polymerization, and bulk polymerization. Of those, solution polymerization in which solvents are employed is preferably carried out from a viewpoint of preventing gelation and capability of homogeneous reaction.

The radical (co)polymerization of the epoxy(meth) acrylate in the present invention is carried out in a temperature range of approximately from 30° to 120° C., preferably from 50° to 100° C., which is a temperature range for carrying out conventional radical (co)polymerization.

As the solvents in the solution polymerization, there may be preferably employed one or more of solvents such as benzene, toluene, and xylene, etc. which are aromatic solvents, methanol, ethanol, and 2-propanol which are alcohols, acetone, methylethyl ketone, and methylisobutyl ketone, etc. which are ketone compounds, diethylether, dibutyl ether, dioxane, etc. which are ether compounds, ethyl acetate, isobutyl acetate, ethyleneglycol monoacetate, and propyleneglycol monoalkyl acetate, etc. which are ester compounds, dimethylformamide and dimethylacetoamide which are amides, chloroform, dimethylchloride, carbon tetrachloride, and chlorobenzen, etc. which are halogenated solvents, etc.

In the case of solution polymerization, solvents are employed in an amount ranging from 0 to 95% by weight, preferably from 60 to 90% by weight based on the total amounts of the monomers.

In the case when it exceeds 95% by weight, although the polymerization is readily carried out, it becomes disadvantageous from a viewpoint of factors concerning productivity such as recovery of the solvents and plant scale.

Thus-obtained (meth)acrylic resin having epoxy group-containing side chains represented by the general formula (1-4) of the present invention is a composition containing a variety of random resin components, and the average molecular weight ranges generally from 500 to 300,000, preferably from 1,000 to 10,000. Furthermore, oxirane oxygen concentration in the resin composition ranges generally from 0.5 to 10% by weight, preferably from 1.0 to 5.0% by weight.

It is to be noted that side chains represented by the general formula (1-4)' are described hereinafter, specifically, in a thermosetting resin composition which is a ninth aspect of the present invention.

According to a ninth aspect of the present invention, there is provided a thermosetting resin composition comprising a (meth)acrylic resin having epoxy group-containing side chains represented by general formula (1-4) and side chains represented by general formula (1-4)'

—COOCR$^{a'}$R$^{b'}$R$^{c'}$    (1-4)

—COOCR$^d$    (1-4)'

wherein R$^{a'}$, R$^{b'}$, and R$^{c'}$ are each an independent hydrogen or substituted group represented by general formula (2-2), R$^d$ is a functional group capable of reacting with epoxy group

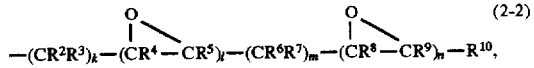

$$-(CR^2R^3)_k-(CR^4-CR^5)_l-(CR^6R^7)_m-(CR^8-CR^9)_n-R^{10}, \quad (2\text{-}2)$$

at least one of R$^{a'}$, R$^{b'}$, and R$^{c'}$ is not hydrogen, R$^2$, R$^6$, R$^7$, and R$^{10}$ are each independently hydrogen or alkyl group having a carbon number of 1 to 10, R$^3$ is independently hydrogen, or an alkyl, alkenyl or epoxy group having a carbon number of 1 to 10, R$^4$, R$^5$, R$^8$ and R$^9$, are each independently hydrogen or alkyl group having a carbon number of 1 to 5, k is an integer of 0 to 30, l is an integer of 0 to 5, m is an integer of 0 to 30, and n is an integer of 1 to 5, and optionally a compound having functional groups capable of reacting with an epoxy group.

According to a tenth aspect of the present invention, there is provided a coating composition containing the thermosetting resin composition.

The thermosetting resin composition of the present invention can be prepared by copolymerization of the epoxy (meth)acrylate represented by the above general formula (1-2) with a polymerizable monomer having a functional group represented by general formula (1-4)' which is capable of reacting with an epoxy group.

Furthermore, the thermosetting resin composition of the present invention can be also prepared by only mixing the (meth)acrylic resin having epoxy group-containing side chains represented by the above general formula (1-4) which is the fourth aspect of the present invention with a compound having functional groups capable of reacting with an epoxy group.

In the case of mixing with a compound having functional groups capable of reacting with an epoxy group, the side chains represented by the above-described general formula (1-4)' are not always essential in the (meth)acrylic resin.

Still further, the thermosetting resin composition of the present invention can be also prepared by mixing the (meth) acrylic resin having epoxy group-containing side chains represented by the above general formula (1-4) with a resin obtained by (co)polymerization of a polymerizable monomer having a functional group represented by general formula (1-4)' which is capable of reacting with an epoxy group.

Also in the case of mixing with the resin obtained by (co)polymerization of a polymerizable monomer having a functional group represented by general formula (1-4)', the side chains represented by the above-described general formula (1-4)' are not always essential in the (meth)acrylic resin.

As practical examples of the functional groups capable of reacting with an epoxy group, there are preferably exemplified carboxylic group, silanol group, hydrolyzable alkoxysilane group, and hydroxyl group.

In the case when the thermosetting resin composition of the present invention is employed as a coating composition, it can be employed as a one-component type or two-component type product.

In the following, there is described a method for introducing the functional groups capable of reacting with an epoxy group into the (meth)acrylic resin having epoxy group-containing side chains represented by the above general formula (1-4).

As the polymerizable monomer to be employed in order to introduce carboxylic groups, there are employed a variety of monomers which are employed in processes of the conventional resins having carboxylic groups, which specifically include monomers having carboxylic group such as acrylic acid, methacrylic acid, fumaric acid, maleic acid, itaconic acid, crotonic acid, a half ester thereof in which anhydride thereof is reacted with an alcohol. In addition to the use of the polymerizable monomers having carboxylic group, a polymer obtained by copolymerization of an unsaturated carboxylic anhydride with other monomers which are starting monomers for preparation of acrylic resins may be also changed to a half ester with an alcohol or a resin having hydroxyl groups.

Furthermore, there can be employed beta-hydroxyalkyl (meth)acrylate such as 2-hydroxyethyl-(meth)acrylate, 2-hydroxypropyl(meth)acrylate, 4-hydroxybutyl(meth) acrylate, a lactone adduct thereof (for example, PCL-FA and PCL-FM, etc., manufactured by Daicel Chemical Industries, Ltd.), etc., and further polymerizable monomers such as an ethyleneoxide or propyleneoxide adducts of (meth)acrylic acid (Blemmer PP and Blemmer PE manufactured by Nihon Yushi, Ltd.) which are monomers having carboxylic group at terminal obtained by adding acid anhydrides to polymerizable monomers having hydroxyl group.

As the acid anhydride, there are exemplified succinic anhydride, phthalic anhydride, tetrahydrophthalic anhydride, hexahydrophthalic anhydride, trimellitic anhydride, a head acid (a derivative having chlorine of phthalic anhydride), hymic anhydride, adipic anhydride, azelaic anhydride, sebacic anhydride, and derivatives thereof.

The monomers having carboxylic group can be readily prepared by heating the polymerizable monomers having hydroxyl group with the acid anhydrides at 60° to 150° C. in the presence of a polymerization initiator.

As components in thermosetting resin composition of the present invention, there are preferably contained 1 to 80% by weight of the epoxy(meth)acrylate represented by the general formula (1-2) and 5 to 60% by weight of the monomers having carboxylic group in the (meth)acrylic resin having epoxy group-containing side chains represented by the general formula (1-4).

The molar ratio of epoxy groups to carboxylic groups generally ranges from 1/0.01 to 1/100, preferably from 1/0.1 to 1/10.

Furthermore, the thermosetting resin composition of the present invention may contain catalysts for the reaction between epoxy groups and carboxylic groups.

As specific examples of the catalysts, there are exemplified quaternary ammonium salts such as benzylethyl ammonium chloride or bromide, tetramethyl ammonium chloride or bromide, tin-based catalysts such as dimethyltin bis (methylmaleate), dimethyltin bis(ethylmaleate), dimethyltin bis(butylmaleate), dibutyltin bis(butylmaleate), phosphorus compounds such as triphenyl phosphine, tetraphenyl phosphonium chloride or bromide.

The catalysts are employed in an amount ranging from 1 ppm to 1%, preferably from 10 ppm to 3,000 ppm based on the total weight of the (meth)acrylic resin having epoxy group-containing side chains represented by the general formula (1-4).

In the following, there is described a process for introducing hydroxyl group which is one of the functional groups capable of reacting with an epoxy group.

The epoxy group in the substituted group represented by the general formula (2-2) can be cured with cationic polymerization catalysts because of a high reactivity in a cationic polymerization compared to conventional compounds having glycidyl group such as glycidylmethacrylate.

As monomers for introducing hydroxyl groups which are one of the functional groups capable of reacting with an epoxy group, there are exemplified a beta-hydroxyalkyl (meth)acrylate such as 2-hydroxyethyl(meth)acrylate, 2-hydroxypropyl-(meth)acrylate, 4-hydroxybutyl (meth) acrylate, a lactone adduct thereof (for example, PCL-FA and PCL-FM, etc., manufactured by Daicel Chemical Industries, Ltd.), etc., and further polymerizable monomers such as an ethyleneoxide or propyleneoxide adducts of (meth)acrylic acid (Blemmer PP and Blemmer PE manufactured by Nihon Yushi, Ltd.).

Furthermore, the thermosetting resin composition of the present invention may preferably contain conventional amine-based, alkali-based and acid-based catalysts for the reaction between epoxy groups and hydroxyl groups.

As specific examples of the alkali-based catalysts, there are exemplified imidazoles such as 4-methylimidazole, tertiary amines such as tris(dimethylamino)phenol, N,N-dimethylbenzylamine, inorganic alkalis such as KOH and NaOH, alcoholates such as sodium alcoholates.

As specific examples of the acid-based catalysts, there are exemplified phosphoric acid or esters thereof, (meth) acrylates having acidic phosphoric acid groups, oxalic acid, succinic acid, trimellitic acid, and p-toluene sulfonic acid which have high acidity and accelerate the cationic polymerization reaction.

The catalysts are employed in an amount ranging from 1 ppm to 10%, preferably from 10 ppm to 2% based on the total weight of the (meth)acrylic resin having epoxy group-containing side chains represented by the general formula (1-4). In the case when it is below 1 ppm, acceleration effect in curing is small, and in the case when it exceeds 10%, properties in cured articles unpreferably decrease.

As components in thermo setting resin composition of the present invention, there are preferably contained 1 to 80% by weight of the epoxy(meth)acrylate represented by the general formula (1-2) and 5 to 60% by weight of the monomers having hydroxyl group in the (meth)acrylic resin having epoxy group-containing side chains represented by the general formula (1-4).

The molar ratio of epoxy groups to hydroxyl groups generally ranges from 1/0.01 to 1/100, preferably from 1/0.1 to 1/10.

Furthermore, in the thermosetting resin composition of the present invention, compounds having silanol group or hydrolyzable alkoxysilyl group are preferably employed together with other monomers, resulting in being capable of improving properties in cured articles.

As specific examples of compounds having hydrolyzable alkoxysilyl group, there are exemplified the compounds having silanol group or hydrolyzable alkoxysilyl group, silane coupling agents such as beta-(3,4-epoxycyclohexyl) ethyl trimethoxysilane, gamma-glycidoxypropyl trimethoxysilane, and gamma-glycidoxypropylmethyl diethoxysilane, which act as crosslinking components.

Furthermore, alkoxysilyl group can be also introduced into the thermosetting resin composition of the present invention using resins obtained by (co)polymerization of a monomer having alkoxysilyl group represented by general formula (4-1)

$$CH_2=CR^1-A-R^2-(SiR^3R^4O)_n-R^5 \quad (4-1)$$

which is described later.

The resins or compounds having hydrolyzable alkoxysilyl groups are preferably introduced in a weight ratio of 5 to 50% by weight based on the total weight of the (meth)acrylic resin having epoxy group-containing side chains represented by the general formula (1-4).

In the following, there is described a process for introducing silanol group or hydrolyzable alkoxysilyl group which is one of the functional groups capable of reacting with an epoxy group into the (meth)acrylic resin having epoxy group-containing side chains represented by the general formula (1-4).

The epoxy group in the substituted group represented by the general formula (2-2) can be cured by silanol group or hydrolyzable alkoxysilyl group with cationic polymerization catalysts because of a high reactivity in a cationic polymerization compared to conventional compounds having glycidyl group such as glycidyl methacrylate.

As polymerizable monomers to be employed for introducing silanol group or hydrolyzable alkoxysilyl group, there are employed the compounds having alkoxysilyl group represented by general formula (4-1)

$$CH_2=CR^1-A-R^2-(SiR^3R^4O)_n-R^5 \quad (4-1)$$

wherein $R^1$ is hydrogen or methyl group, —A— is —COO— or —COO— $C_6H_4$—, $R^2$ is a divalent aliphatic hydrocarbon residual group having a carbon number of 1 to 6, $R^3$ and $R^4$ is independently phenyl group, alkyl group having a carbon number of 1 to 6, alkoxyl group having a carbon number of 1 to 6, and hydroxyl group, $R^5$ is hydrogen, phenyl group, alkyl group having a carbon number of 1 to 6, and alkoxyl group having a carbon number of 1 to 6, n is an integer of 1 to 20, and the unit —(SiR³R⁴O)ₙ— also includes a structure in which silicone is three-dimensionally extended by siloxane bonds.

Specifically, there are employed gamma-(meth) acryloxypropyl trimethoxysilane, gamma-(meth) acryloxypropyl triethoxysilane, gamma-(meth)acryloxypropyl tripropoxysilane, gamma-(meth) acryloxypropylmethyl dimethoxysilane, gamma-(meth) acryloxypropylmethyl diethoxysilane, gamma-(meth) acryloxypropylmethyl dipropoxysilane, gamma-(meth) acryloxybutylphenyl dimethoxysilane, gamma-(meth) acryloxybutylphenyl diethoxysilane, gamma-(meth) acryloxybutylphenyl dipropoxysilane, gamma-(meth) acryloxyproyldimethyl methoxysilane, gamma-(meth) acryloxyproyldimethyl ethoxysilane, gamma-(meth) acryloxyproylphenylmethyl methoxysilane, gamma-(meth) acryloxyproylphenylmethyl ethoxysilane.

Furthermore, there are employed the following compounds

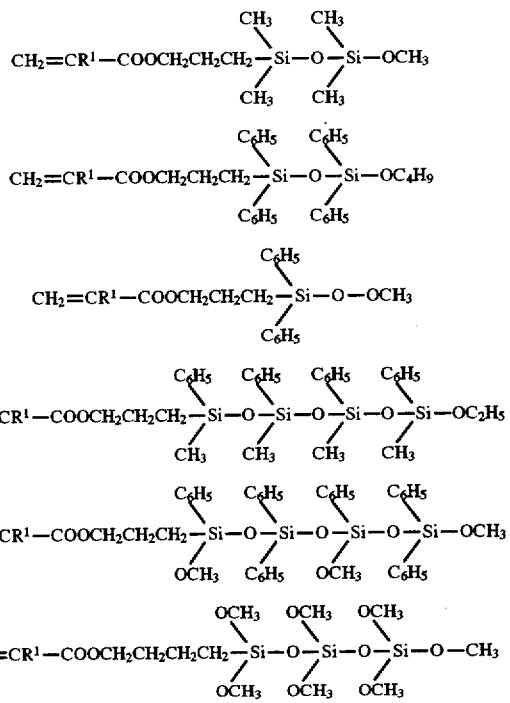

wherein $R^1$ is a hydrogen or an alkyl group having carbon number of 1 to 6.

Of the compounds having alkoxysilyl group represented by the general formula (4-1), as compounds having carbonyloxyphenylene group in the unit —A—, there are exemplified the following compounds

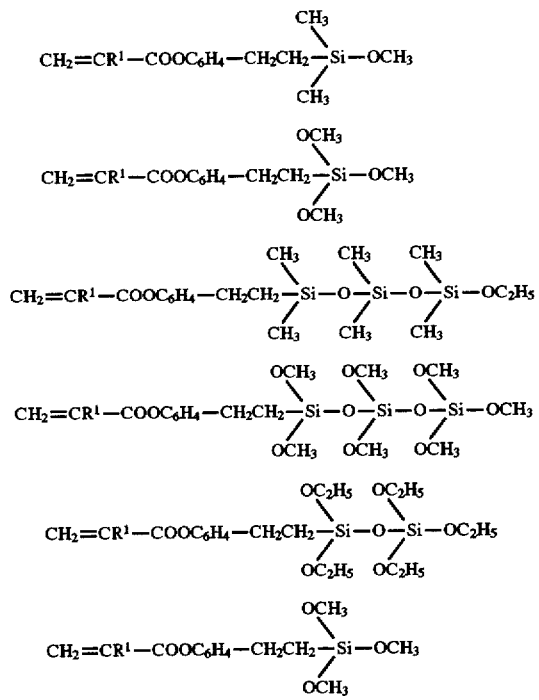

wherein $R^1$ is a hydrogen or an alkyl group having carbon number of 1 to 6.

In the thermosetting resin composition of the present invention, the compounds having silanol group or hydrolyzable alkoxysilyl group is introduced into the (meth) acrylic resin having epoxy group-containing side chains represented by the general formula (1-3) in the ratio of 1/0.1 to 1/1000, preferably from 1/0.25 to 1/100 with respect to the epoxy(meth)acrylate represented by the general formula (1-2).

In the case when the ratio of the epoxy(meth)acrylate represented by the general formula (1-2) exceeds 1000, curability of the composition decreases, and in the case when it is below 0.1, properties in cured articles and curing velocity decrease, and shrinkage in the cured articles occasionally is caused.

In the thermosetting resin composition of the present invention, there may be employed conventional catalysts such as aluminum chelate compounds, titanium chelate compounds, and zirconium chelate compounds in order to accelerate the cationic polymerization reaction between epoxy groups and silanol groups or hydrolyzable alkoxysilanol groups in the (meth)acrylic resin having epoxy group-containing side chains represented by the general formula (1-3). The chelate compounds can give an appropriate pot-life.

Of the chelate compounds, there are preferred chelate compounds having a compound capable of forming a keto or enol tautomer as ligand forming a stable chelate ring.

As the compounds capable of forming the keto or enol tautomer, there can be employed beta-diketones such as acetylacetone, acetoacetic acid esters such as methyl acetoacetate, malonic acid esters such as ethyl maloate, ketones having hydroxyl group at beta position such as diacetonealcohol, aldehydes having hydroxyl group at beta position such as salicyclic aldehyde, and esters having hydroxyl group at beta position such as methyl salicylate, etc. Of those, acetoacetic acid esters and beta-diketones are preferred.

Aluminum chelate compounds can be prepared by mixing 1 mol of an aluminum alcoholate represented by R—O—Al(OR)—O—R [wherein R is an alkyl group or alkenyl group having a carbon number of 1 to 20 which may be identical or different from each other] with approximately 3 mol or less of the compound capable of forming the above-described keto or enol tautomer, optionally followed by heating.

As the aluminum alcoholate represented by R—O—Al(OR)—O—R, there are exemplified aluminum trimethoxide, aluminum trietho-xide, aluminum tri-n-propoxide, aluminum triisopropoxide, aluminum tri-n-butoxide, aluminum tri-n-isobutoxide, aluminum tri-sec-butoxide, and aluminum tri-tert-butoxide, etc. Of those, there are preferred aluminum triisopropoxide, aluminum tri-sec-butoxide, and aluminum tri-n-butoxide.

Titanium chelate compounds can be prepared by mixing 1 mol of an titanium alcoholate represented by R—O—[Ti(OR)$_2$—O]$_m$—Ti(OR)$_2$—OR [wherein R is an alkyl group or alkenyl group having a carbon number of 1 to 20 which may be identical or different from each other, and m is an integer of 0 to 20] with approximately 3 mol or less of the compound capable of forming the above-described keto or enol tautomer, optionally followed by heating.

As the titanium alcoholate represented by R—O—[Ti(OR)$_2$—O]$_m$—Ti(OR)$_2$—OR, there are exemplified tetramethyltitanate, tetraethyltitanate, tetra-n-propyltitanate, tetraisoproyltitanate, tetra-n-butyltitanate, tetraisobutyltitanate, tetra-tert-butyltitanate, tetra-n-pentyltitanate, tetra-n-hexyltitanate, tetraisooctyltitanate, and tetra-n-lauryltitanate, etc.

Of those, there are preferred tetraisoproyltitanate, tetra-n-butyltitanate, and tetra-tert-butyltitanate.

In the case of compounds in which m exceeds 1, there are preferred from respective dimers to respective dodecamers of tetraisobutyltitanate, tetra-tert-butyltitanate, tetraisoproyltitanate, and tetra-n-butyltitanate.

Zirconium chelate compounds can be prepared by mixing 1 mol of an zirconium compound represented by R—O—[Zr(OR)$_2$—O]$_m$—Zr(OR)$_2$—OR [wherein R is an alkyl group or alkenyl group having a carbon number of 1 to 20 which may be identical or different from each other, and m is an integer of 0 to 20] with approximately 4 mol or less of the compound capable of forming the above-described keto or enol tautomer, optionally followed by heating.

As the zirconates represented by R—O—[Zr(OR)$_2$—O]$_m$—Zr(OR)$_2$—OR, there are exemplified tetraethylzirconate, tetra-n-propylzirconate, tetraisopropylzirconate, tetraisobutylzirconate, tetra-n-butylzirconate, tetra-secbutylzirconate, tetra-tert-butylzirconate, tetra-n-pentylzirconate, tetra-tert-pentylzirconate, tetra-terthexylzirconate, tetra-n-heptylzirconate, tetra-n-octylzirconate, and tetra-n-stearylzirconate.

Of those, there are preferred tetraisopropylzirconate, tetra-n-propylzirconate, tetraisobutylzirconate, tetra-n-butylzirconate, tetra-sec-butylzirconate, and tetra-tert-butylzirconate.

In the case of compounds in which m exceeds 1, there are preferred from respective dimers to respective dodecamers of tetraisopropylzirconate, tetra-n-propylzirconate, tetra-n-butylzirconate, tetraisobutylzirconate, tetra-sec-butylzirconate, and tetra-tert-butylzirconate. Furthermore, there may be contained associate compounds of the zirconates.

Of the chelate compounds described hereinabove in the present invention, there are particularly preferred diisopropylate ethylacetoacetate aluminum, tris(ethylacetoacetate) aluminum, tris(n-propylacetoacetat)aluminum, tris(isopropylacetoacetate)aluminum, tris(n-butylacetoacetate) aluminum, isopropoxybisethyl acetoacetate aluminum, diisopropoxybisethyl acetoacetate aluminum, tris(acetylacetonate)aluminum, tris(ethylacetonate) aluminum, diisopropylate ethylacetonate aluminum, monoacetylacetonate aluminum, bis(ethylacetonate) aluminum, monoethylacetoacetate bis(acetylacetonat)aluminum, tris(isopropylate)aluminum, tris(sec-butylate)aluminum, diisopropylate mono-secbutoxyaluminum, and tris(acetylacetone) aluminum.

Furthermore, there are preferred titanium chelate compounds such as diisopropoxy bis(ethylacetoacetate) titanium, diisopropoxy bis(acetylacetate)titanium, and diisopropoxy bis(acetylacetone)titanium.

Still further, there are preferred zirconium chelate compounds such as tetrakis(acetylacetone)zirconium, tetrakis(n-propylacetoacetate)zirconium, tetrakis(acetylacetonate) zirconium, and tetrakis(ethylacetonate)zirconium. There may be employed one or more of the above-described aluminum compounds titanium compounds, and zirconium compounds.

The chelate compounds are employed in the amount ranging from 0.01 to 30 parts by weight, preferably from 0.05 to 15 parts by weight, and more preferably from 0.5 to 10 parts by weight based on the total weight of the (meth) acrylic resins.

In the case when the amount is below 0.01 part by weight, curing by crosslinking is insufficient and, on the contrary, in the case when it exceeds 30 parts by weight, the catalysts remained in cured articles decrease properties such as, for example, water absorption property and weatherability, etc. of the cured articles.

In the case when the thermosetting resin composition of the present invention is employed as a coating composition, there may be mixed melamine-formaldehyde resins and/or isocyanate compounds and blocked isocyanates in order to increase crosslinking density.

It is to be noted that there may be preferably employed at least two of the functional groups capable of reacting with epoxy group in the (meth)acrylic resin having epoxy group-containing side chains represented by general formula (1-3).

The (meth)acrylic resin having epoxy group-containing side chains represented by general formula (1-3) in the thermosetting resin composition of the present invention has a number average molecular weight of from 1,000 to 100,000, preferably from 2,000 to 50,000 on an average.

In the case when the molecular weight is below 1,000, mechanical properties in cured articles are not sufficient, and in the case when it exceeds 100,000, a viscosity considerably increases, resulting in lowering workability.

In the thermosetting resin composition of the present invention, there may be mixed other epoxy compounds having a molecular weight below 3,000.

The other epoxy compounds having a low molecular weight are effective for decreasing a viscosity of the thermosetting resin composition of the present invention, which effectively act as a reactive diluent.

The other epoxy compounds can be mixed in the amount of from 1 to 80% by weight, preferably from 5 to 60% by weight based on the total weight of resin components in the thermosetting resin composition.

In the case when it is below 1%, the effect for decreasing viscosity is insufficient, and in the case when it exceeds 80%, properties in cured articles are deteriorated.

Still further, in the thermosetting resin composition of the present invention, there may be also mixed other components having oxirane ring(s) and a molecular weight below 1,500 which are a diluent having reactivity.

Use of the reactive diluent enables to decrease a use amount of solvents for diluting which are discharged at working circumstances during curing.

As the diluent having reactivity which has a low molecular weight, there are employed a bifunctional alicyclic compound (e.g. 3,4-epoxycyclohexyl-3,4-cyclohexanecarboxylate such as Celloxide 2021 and 2080-family manufactured by Daicel Chemical Industries, Ltd. and ERL 4221 manufactured by Union Carbide Co., etc.), a multifunctional alicyclic compound (e.g. Epolead GT-family manufactured by Daicel Chemical Industries, Ltd.), an alkoxysilane compound of 1,9-nonanediepoxide and 1,9-nonanemonoepoxide, a glycidyl group-containing epoxy monomer such as diglycidylether of bisphenol A, diglycidylether of hydrogenated bisphenol A, diglycidylether of cyclohexanedimethanol.

According to an eleventh aspect of the present invention, there is provided a powder coating composition which comprises (A) a (meth)acrylic resin having epoxy group-containing side chains represented by general formula (1-4)

—COOCR$^{a'}$R$^{b'}$R$^{c'}$ (1-4)

wherein R$^{a'}$, R$^{b'}$, and R$^{c'}$ are each independently hydrogen or substituted group represented by general formula (2-2)

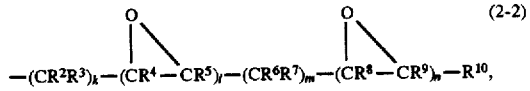

$$-(CR^2R^3)_k-(CR^4=CR^5)_l-(CR^6R^7)_m-(CR^8-CR^9)_n-R^{10},$$ (2-2)

at least one of R$^{a'}$, R$^{b'}$, and R$^{c'}$ is not hydrogen, R$^2$, R$^6$, R$^7$, and R$^{10}$ are each independently hydrogen or alkyl group having a carbon number of 1 to 10, R$^3$ is independently hydrogen, or an alkyl, alkenyl or epoxy group having a carbon number of 1 to 10, R$^4$, R$^5$, R$^8$ and R$^9$, are each independently hydrogen or alkyl group having a carbon number of 1 to 5, k is an integer of 0 to 30, l is an integer of 0 to 5, m is an integer of 0 to 30, and n is an integer of 1 to 5 and (B) a curing agent having carboxylic groups.

A powder coating composition of the present invention includes the (meth)acrylic resin having epoxy group-containing side chains represented by general formula (1-4) of the seventh aspect described hereinabove and a curing agent having carboxylic groups.

The (meth)acrylic resin having epoxy group-containing side chains represented by the general formula (1-4) has preferably an epoxy equivalent of from 100 to 2,000 and an average molecular weight of from 300 to 2,000, preferably from 500 to 10,000. Also, the curing agent having carboxylic groups is preferably a multifunctional carboxylic acid having a molecular weight of below 500 or a carboxylic group-containing polyester resin having an acid value of 15 to 200 mgKOH/g and a softening point of 70° to 160° C.

In the case when the molecular weight is below 300, mechanical strength in the coating layer becomes insufficient and, contrarily, in the case when it exceeds 20,000, fluidity of the coating in kneading and baking becomes inferior, resulting in deteriorating a clarity and smoothness of the coating layer.

Furthermore, in the case when a carboxylic group-containing polyester resin is employed as a curing agent, a compatibility of the (meth)acrylic resin having epoxy group-containing side chains with the polyester becomes inferior, resulting in insufficient crosslinking reaction and insufficient properties of the coating layer.

In the component (A) a (meth)acrylic resin having epoxy group-containing side chains represented by the general formula (1-4), the epoxy(meth)acrylate represented by general formula (1-2) is employed in a ratio of from 5 to 100% by weight, preferably from 10 to 90% by weight, and more preferably from 10 to 70% by weight.

In the case when the ratio is below 5% by weight, kneading time cannot be extended in the for powder coating composition compared to conventional powder coating compositions using a compound having glycidyl group, and flow properties in coating before baking are insufficient.

Furthermore, in the case when a carboxylic group-containing polyester resin is employed as a curing agent, a compatibility of the (meth)acrylic resin having epoxy group-containing side chains with the polyester becomes inferior, resulting in insufficient properties of the coating layer.

As the preferred copolymerizable monomers to be copolymerized with the epoxy(meth)acrylate represented by the general formula (1-2), there are exemplified styrene, (meth) acrylates, fumaric diester, acrylonitrile, and acrylamide, etc. Of those, methylmethacrylate which is one of (meth) acrylates is particularly preferred from a viewpoint of Tg and weatherability.

As the curing agent having carboxylic groups which is the component (B) of the present invention, there can be preferably employed a compound having a chemical formula R—(COOH)$_n$ [wherein R is an alkylene group having a straight chain or branched chain having a carbon number of 1 to 25, an alicyclic alkyl group, an aromatic group, and a cyclic ring having a plurality of elements, and n is a integer of 2 to 5].

Specifically, there are exemplified succinic acid, adipic acid, pimelic acid, suberic acid, azelaic acid, sebacic acid, decanedicarboxylic acid, malonic ester, phthalic acid, trimellitic acid, pyromellitic acid, benzophenone tetracarboxylic acid, ethyleneglycol bis(trimellitate), glyceroltris (trimellitate), tetrahydrocarboxylic acid, methyltetrahydrocarboxylic acid, nadic acid, alkenyl succinic acid, hexahydrophthalic acid, methylhexahydrophthalic acid, methylcyclohexene tetracarboxylic acid, a dimer acid, and triscarboxyethyl isocyanurate, etc.

Furthermore, as the curing agent having carboxylic groups which is the component (B) of the present invention, there can be also preferably employed a polyester resin having carboxylic groups at terminals.

Although conventional (meth)acrylic resins having epoxy groups using glycidyl methacrylate are poor in a compatibility with the polyester resin having carboxylic groups at terminals, the (meth)acrylic resin having epoxy group-containing side chains represented by the general formula (1-4) which is the component (A) in a powder coating composition of the present invention is very excellent in compatibility with the polyester resin, resulting in being capable of providing coating layers having excellent properties.

The polyester resin having carboxylic groups at terminals has preferably an acid value ranging from 15 to 200 mgKOH/g, a softening point ranging from 70° to 160° C., more preferably from 100° to 130° C., and number average molecular weight ranging from 500 to 20,000, more preferably from 1,000 to 15,000.

Although the polyester resin may have a branched, linear, and mixed structure thereof, linear structure not having branched structure so much is more preferred from viewpoint of fluidity in melting, outer appearances of coating layers after baking, and gloss of the coating layers.

The polyester resin having carboxylic groups at terminals can be limitlessly prepared by the esterification between polybasic acids or anhydrides thereof and polyols using conventional catalysts.

As the polybasic acids or anhydrides to be employed for the preparation of the polyester resin, there are exemplified terephthalic acid, isophthalic acid, methylterephthalic acid, trimellitic acid, pyromellitic acid, and anhydrides or alkyl esters thereof, adipic acid, sebacic acid, succinic acid, maleic acid, fumaric acid, tetrahydrophthalic acid, methyltetrahydrophthalic acid, hexahydrophthalic acid, methylhexahydrophthalic acid, and anhydrides or alkyl esters thereof.

As the polyols to be employed for the preparation of the polyester resin, there are exemplified ethyleneglycol, propyleneglycol, 1,3-butanediol, 1,4-butanediol, 1,6-hexanediol, neopentylglycol, bishydroxyethyl terephthalate, hydrogenated bisphenol A, ethyleneglycol adducts of hydrogenated bisphenol A, propyleneglycol adducts of hydrogenated bisphenol A, trimethylolpropane, trimethylolethane, glycerine, pentaerythritol, 2,2,4-trimethylpentane-1,3-diol, monoepoxides such as alpha-olefinmonoepoxide, etc.

Furthermore, there can be employed lactone polyols derived from cyclic lactones and the above-described polyols. As the cyclic lactones, there are employed epsilon-caprolactone, 4-methylcaprolactone, 2-methylcaprolactone, delta-valerolactone, beta-methyl-delta-valerolactone, beta-propiolactone, and gamma-butyrolactone, etc. There may be employed one or more of lactones.

(n+1) mol of the polybasic acids are allowed to react with n mol of the polyols to prepare the polyester resin having carboxylic groups at terminals.

The esterification between the polybasic acids or anhydrides thereof and the polyols is carried out in a temperature ranging from 130° to 240° C., preferably from 140° to 230° C. while streaming an inert gas such as nitrogen gas, etc., whereby there can be preferably prevented deterioration and coloring of a resulting polyester resin by oxidation.

The esterification is carried out in the presence of catalysts.

Specific examples of the catalysts, there are exemplified tin compounds such as stannous octylate, dibutyltin dilaurate, monobutyltin oxide, dibutyltin oxide, monobutyltin hydroxybutyloxide, and stannous chloride, etc., titanium compounds such as tetrabutyl titanate, tetraethyl titanate, and tetraisopropyl titanate, etc.

The catalysts are employed in an amount ranging from 0.1 ppm to 1000 ppm, preferably from 1 ppm to 100 ppm based on the total amount of starting materials. In the case when it exceeds 1000 ppm, a product unpreferably colors and a stability in a product is adversely affected. On the contrary, in the case when it is below 0.1 ppm, the esterification velocity becomes unpreferably slow.

Thus-obtained polyester resin having carboxylic groups at terminals is mixed with the (meth)acrylic resin having epoxy group-containing side chains represented by the general formula (1-4) to prepare the powder coating composition of the present invention.

In the powder coating composition of the present invention, the equivalent ratio of epoxy groups to carboxylic groups is 0.5 to 2.0, preferably 0.7 to 1.4.

In the case when the equivalent ratio is below 0.5 or exceeds 2.0, curing velocity becomes exceedingly slow, and there can not be obtained cured coating layers having sufficient properties.

In order to prepare the powder coating composition of the present invention, the component (A) which is a (meth)acrylic resin having epoxy group-containing side chains and the component (B) which is a curing agent are mixed with pigments, silicone compounds, fluidity controlling agents such as a polymer of 2-ethylhexylacrylate, amine-based or phosphoric acid-based catalysts for curing such as tertiary amine compounds, quaternary amine compounds, triphenyl phosphine, and phosphonium salts, etc., and further other additives, followed by kneading by an extruder, etc., crushing and classifying.

The powder coating composition of the present invention can be coated with electrostatic coating methods or flowing bed coating methods which are conventional methods.

In the following, although the present invention is specifically illustrated below by Examples, it is not limited.

EXAMPLE 1

<Preparation of a methacrylate having alkenyl group represented by the general formula (1-1)>

A teardrop type flask equipped with a stirrer, a tube for blowing air, a tube for removing water, and a reflux condenser was charged with 600 parts by weight of oleic alcohol having a hydroxyl value of 213 (the trade name, UNJECOL-90N manufactured by Shin-Nihon Rika, Ltd.), 392 parts by weight of methacrylic acid, 400 parts by weight of n-heptane, 1.0 part by weight of p-toluene sulfonic acid, and 4.96 parts by weight of hydroquinone monomethylether, followed by carrying out esterification reaction accompanied by dehydration at 120° C.

The reaction was carried out for approximately 9 hours. After the completion of the reaction, a reaction crude solution was washed with an aqueous alkali solution and then washed with water twice in order to remove unreacted methacrylic acid and p-toluene sulfonic acid. Subsequently, low boiling point ingredients were removed with an evaporator while blowing air to obtain 749 parts by weight of a methacrylate.

Delta values of ¹H-NMR related to the methacrylate are shown below.

Delta (ppm)

Vicinity of 0.8–1.0 (3.0H): proton in terminated —$CH_3$

Vicinity of 1.2–1.7 (26H): proton in long chain —$CH_2$—

Vicinity of 1.95–2.1 (6.2H): proton in —$CH_3$ of methacrylic group and proton in —$CH_2$— adjacent to double bond carbon Vicinity of 4.1–4.2 (2.0H): proton in —$CH_2$— group bonded to oxygen atom of ester bond Vicinity of 5.3–5.5 (1.7H): proton in $CH_2$=

Vicinity of 5.5–5.6 (1.0H): one proton in $CH_2$= in methacrylic group

Vicinity of 6.1–6.2 (1.0H): one proton in $CH_2$= in methacrylic group

It was identified that the methacrylate has the following chemical formula.

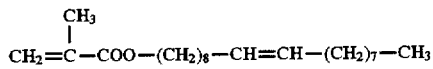

EXAMPLE 2

<Preparation of a methacrylate having alkenyl group represented by the general formula (1-1)>

A teardrop type flask equipped with a stirrer, a tube for blowing air, a tube for removing water, and a reflux condenser was charged with 400 parts by weight of 3-methyl-3-butene-1-ol (a trade name, Isoprenol manufactured by Kuraray, Ltd.), 800 parts by weight of methacrylic acid, 400 parts by weight of n-heptane, 1.2 parts by weight of monobutyltin oxide, and 6.0 parts by weight of hydroquinone monomethylether, followed by carrying out esterification reaction accompanied by dehydration at 120° C.

The reaction was carried out for approximately 12 hours. After the completion of the reaction, a reaction crude solution was washed with an aqueous alkali solution and then washed with water twice in order to remove unreacted methacrylic acid, etc. Subsequently, low-boiling-point ingredients were removed with an evaporator while blowing air to obtain 507.1 parts by weight of a methacrylate. Delta values of ¹H-NMR related to the methacrylate are shown below.

Delta (ppm)

Vicinity of 1.7–1.8 (3.0H): proton in —$CH_3$ bonded to double bond carbon

Vicinity of 1.95 (3.0H): proton in —$CH_3$ of methacrylic group

Vicinity of 2.3–2.5 (2.0H): proton in —$CH_2$— adjacent to double bond carbon

Vicinity of 4.2–4.3 (2.0H): proton in —$CH_2$— group bonded to oxygen atom of ester bond Vicinity of 4.7–4.9 (1.0H): proton in $CH_2$=

Vicinity of 5.5–5.6 (1.0H): one proton in $CH_2$= in methacrylic group

Vicinity of 6.1–6.2 (1.0H): one proton in $CH_2$= in methacrylic group

By the values, it is identified that 3-methyl-3-butenyl of methacrylic acid was obtained which is a desired product having the following chemical formula.

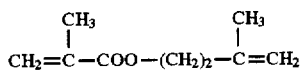

EXAMPLE 3

<Preparation of a methacrylate having alkenyl group represented by the general formula (1-1)>

A teardrop type flask equipped with a stirrer, a tube for blowing air, a tube for removing water, and a reflux condenser was charged with 400 parts by weight of 3-methyl-2-butene-1-ol (a trade name, Prenol manufactured by Kuraray, Ltd.), 800 parts by weight of methacrylic acid, 400 parts by weight of n-heptane, 1.2 parts by weight of titanium tetrabutoxide, and 6.0 parts by weight of hydroquinone monomethylether, followed by carrying out esterification reaction accompanied by dehydration at 120° C. The reaction was carried out for approximately 12 hours. After the completion of the reaction, a reaction crude solution was washed with an aqueous alkali solution and then washed with water twice in order to remove unreacted methacrylic acid, etc. Subsequently, low-boiling-point ingredients were removed with an evaporator while blowing air to obtain 555.9 parts by weight of a product. Delta values of ¹H-NMR related to the product are shown below.

Delta (ppm)

Vicinity of 1.7–1.8 (6.0H): proton in —$CH_3$ bonded to double bond carbon

Vicinity of 1.95 (3.0H): proton in —$CH_3$ of methacrylic group

Vicinity of 4.6–4.7 (2.0H): proton in —$CH_2$— group bonded to oxygen atom of ester bond Vicinity of 5.3–5.5 (1.0H): one proton in $CH_2$= in methacrylic group Vicinity of 5.5–5.6 (1.0H): one proton in $CH_2$= in methacrylic group Vicinity of 6.1–6.2 (1.0H): one proton in $CH_2$= in methacrylic group By the values, it is identified that 3-methyl-2-butenyl of methacrylic acid was obtained which is a desired product having the following chemical formula.

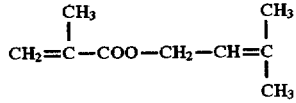

EXAMPLE 4

<Preparation of a methacrylate having alkenyl group represented by the general formula (1-1)>

A teardrop type flask equipped with a stirrer, a tube for blowing air, a tube for removing water, and a reflux condenser was charged with 250 parts by weight of 7-octene-1-ol (a trade name, 7-OEA manufactured by Kuraray, Ltd.), 205 parts by weight of methacrylic acid, 200 parts by weight of n-heptane, 0.46 g of p-toluene sulfonic acid, and 1.35 g of hydroquinone monomethylether, followed by carrying out esterification reaction accompanied by dehydration at 120°C. The reaction was carried out for approximately 9 hours. After the completion of the reaction, a reaction crude solution was washed with an aqueous alkali solution and then washed with water twice in order to remove unreacted methacrylic acid, etc.

Subsequently, low-boiling-point ingredients were removed with an evaporator while blowing air to obtain 361.0 parts by weight of a product. Delta values of $^1$H-NMR related to the product are shown below.

Delta (ppm)

Vicinity of 1.2–1.85 (10H): proton in —$CH_2$— group

Vicinity of 2.0–2.1 (2.0H): proton in —$CH_2$— adjacent to vinyl group

Vicinity of 1.95 (3.0H): proton in —$CH_3$ of methacrylic group

Vicinity of 4.1–4.2 (2.1H): proton in —$CH_2$— group bonded to oxygen atom of ester bond Vicinity of 4.9–5.1 (1.6H): proton in $CH_2$= of vinyl group Vicinity of 5.5–5.6 (1.0H): one proton in $CH_2$= in methacrylic group Vicinity of 5.7–5.9 (0.8H): proton in —CH= of vinyl group Vicinity of 6.1–6.2 (1.0H): one proton in $CH_2$= in methacrylic group By the values, it is identified that 7-octenyl of methacrylic acid was obtained which is a desired product having the following chemical formula.

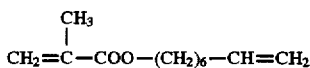

EXAMPLE 5

<Preparation of a methacrylate having alkenyl group represented by the general formula (1-1)>

A teardrop type flask equipped with a stirrer, a tube for blowing air, a tube for removing water, and a reflux condenser was charged with 378 parts by weight of 2,7-octadienol (a trade name, ODA manufactured by Kuraray, Ltd.), 310 parts by weight of methacrylic acid, 200 parts by weight of n-heptane, 2.1 g of p-toluene sulfonic acid, and 3.4 g of hydroquinone monomethylether, followed by carrying out esterification reaction accompanied by dehydration at 120° C. The reaction was carried out for approximately 9 hours. After the completion of the reaction, a reaction crude solution was washed with an aqueous alkali solution and then washed with water twice in order to remove unreacted methacrylic acid, etc.

Subsequently, low-boiling-point ingredients were removed with an evaporator while blowing air to obtain 489.8 parts by weight of a product.

Delta values of $^1$H-NMR related to the product are shown below.

It was identified that the product has the following chemical formula.

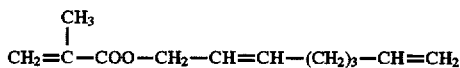

EXAMPLE 6

<Preparation of an acrylate having alkenyl group represented by the general formula (1-1)>

A teardrop type flask equipped with a stirrer, a tube for blowing air, a tube for removing water, and a reflux condenser was charged with 250 parts by weight of 7-octene-1-ol (a trade name, 7-OEA manufactured by Kuraray, Ltd.), 169 parts by weight of acrylic acid, 200 parts by weight of n-heptane, 0.42 g of p-toluene sulfonic acid, and 1.26 g of hydroquinone monomethylether, followed by carrying out esterification reaction accompanied by dehydration at 1200°C. The reaction was carried out for approximately 9 hours. After the completion of the reaction, a reaction crude solution was washed with an aqueous alkali solution and then washed with water twice in order to remove unreacted acrylic acid, etc.

Subsequently, low-boiling-point ingredients were removed with an evaporator while blowing air to obtain 318.2 parts by weight of a product.

Delta values of $^1$H-NMR related to the product are shown below.

Delta (ppm)

Vicinity of 1.2–1.85 (10H): proton in —$CH_2$— group

Vicinity of 2.0–2.1 (2.0H): proton in —$CH_2$— adjacent to vinyl group

Vicinity of 4.1–4.2 (2.1H): proton in —$CH_2$— group bonded to oxygen atom of ester bond Vicinity of 4.9–5.1 (1.6H): proton in $CH_2$= of vinyl group Vicinity of 6.0–6.2 (1.0H): proton in —CH= of acrylic group Vicinity of 6.3–6.5 (1.0H): one proton in $CH_2$= in acrylic group By the values, it is identified that 7-octenyl of acrylic acid was obtained which is a desired product having the following chemical formula.

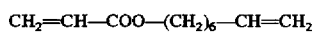

EXAMPLE 7

<Preparation of a methacrylate having alkenyl group represented by the general formula (1-1)>

A 2L-teardrop type flask equipped with a stirrer, a tube for blowing air, a tube for removing water, and a reflux condenser was charged with 400 parts by weight of 1,7-octadiene-3-ol, 328 parts by weight of methacrylic acid, 200 parts by weight of n-heptane, 0.73 part of p-toluene sulfonic acid, and 2.18 part of hydroquinone monomethylether, followed by carrying out esterification reaction accompanied by dehydration at 120° C. The reaction was carried out for approximately 8 hours. After the completion of the reaction, a reaction crude solution was washed with an aqueous alkali solution and then washed with water twice in order to remove unreacted methacrylic acid, etc.

Subsequently, low-boiling-point ingredients were removed with an evaporator while blowing air to obtain 575 parts by weight of a product. It is identified that the product has the following chemical formula.

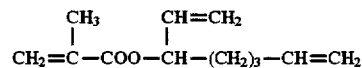

EXAMPLE 8

<Preparation of an acrylate having alkenyl group represented by the general formula (1-1)>

A 2L-teardrop type flask equipped with a stirrer, a tube for blowing air, a tube for removing water, and a reflux condenser was charged with 400 parts by weight of 2,7-octadienol (a trade name of ODA manufactured by Kuraray, Ltd.), 274 parts by weight of acrylic acid, 200 parts by weight of n-heptane, 0.67 part of p-toluene sulfonic acid, and 2.02 part of hydroquinone monomethylether, followed by carrying out esterification reaction accompanied by dehydration at 120° C. The reaction was carried out for approximately 8 hours. After the completion of the reaction, a reaction crude solution was washed with an aqueous alkali solution and then washed with water twice in order to remove unreacted acrylic acid, etc.

Subsequently, low-boiling-point ingredients were removed with an evaporator while blowing air to obtain 526 parts by weight of a product.

It is identified that the product has the following chemical formula.

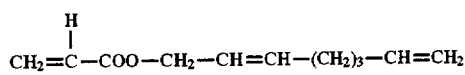

EXAMPLE 9

<Preparation of an epoxymethacrylate represented by the general formula (1-2)>

A jacketed-reaction vessel equipped with a reflux condenser, thermometer, and an agitator having blades was charged with 500 parts by weight of the methacrylate having an alkenyl group represented by the following chemical formula

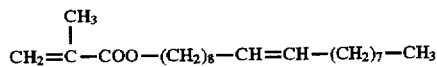

and 0.5 parts by weight of hydroquinone monomethylether, followed by carrying out epoxidation reaction by adding dropwise 370.3 parts by weight of an ethyl acetate solution containing 29.6% of peracetic acid and 0.16 part by weight of potassium pyrophosphate while blowing air.

The reaction was carried out at 40° C. for 4.5 hours, and further aging was carried out for 2 hours. After the completion of the reaction, a reaction crude solution was washed with water thrice. Subsequently, low-boiling-point ingredients were removed with an evaporator to obtain 488.8 parts by weight of an epoxymethacrylate. Delta values of $^1$H-NMR related to the epoxymethacrylate are shown below.
Delta (ppm)
Vicinity of 0.8–1.0 (3.0H): proton in terminated —$CH_3$
Vicinity of 1.2–1.8 (30.0H): proton in $CH_2$ chain
Vicinity of 1.95 (3.0H): proton in —$CH_3$ of methacrylic group
Vicinity of 2.6–2.7 and Vicinity of 2.8–3.0 (1.8H): proton in epoxy group
Vicinity of 4.1–4.2 (2.1H): proton in —$CH_2$— group bonded to oxygen atom of ester bond It was identified that the epoxymethacrylate has the following chemical formula which is a desired product.

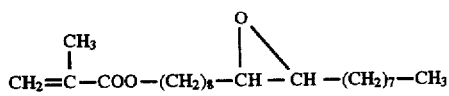

EXAMPLE 10

<Preparation of an epoxymethacrylate represented by the general formula (1-2)>

A jacketed-reaction vessel equipped with a reflux condenser, thermometer, and an agitator having blades was charged with 400 parts by weight of the methacrylate having an alkenyl group represented by the following chemical formula

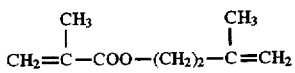

and 0.4 part by weight of hydroquinone monomethylether, followed by carrying out epoxidation reaction by adding dropwise 800.3 parts by weight of an ethyl acetate solution containing 29.6% of peracetic acid and 0.40 part by weight of potassium pyrophosphate while blowing air.

The reaction was carried out at 40° C. for 4.5 hours, and further aging was carried out for 4 hours. After the completion of the reaction, a reaction crude solution was washed with water thrice. Subsequently, low-boiling-point ingredients were removed with an evaporator to obtain 308.6 parts by weight of an epoxymethacrylate. Delta values of $^1$H-NMR related to the epoxymethacrylate are shown below.
Delta (ppm)
Vicinity of 1.4 (3.0H): proton in —$CH_3$ bonded to epoxy group
Vicinity of 1.8–2.0 (3.0H): proton in —$CH_3$ of methacrylic group and proton in —$CH_2$ adjacent to epoxy group
Vicinity of 2.6–2.7 (2.0H): proton in —$CH_2$— of epoxy group
Vicinity of 4.2–4.4 (2.0H): proton in —$CH_2$— group bonded to oxygen atom of ester bond
Vicinity of 5.6 (1.0H): one proton in $CH_2$= in methacrylic group
Vicinity of 6.1 (1.0H): one proton in $CH_2$= in methacrylic group By the values, it is identified that 3-methyl-3,4-epoxy butylmethacrylate was obtained which is a desired product having the following chemical formula.

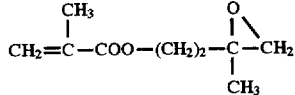

EXAMPLE 11

<Preparation of an epoxymethacrylate represented by the general formula (1-2)>

A jacketed-reaction vessel equipped with a reflux condenser, thermometer, and an agitator having blades was charged with 400 parts by weight of the methacrylate having an alkenyl group represented by the following chemical formula

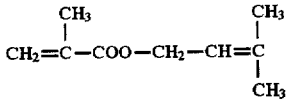

and 0.4 part by weight of hydroquinone monomethylether, followed by carrying out epoxidation reaction by adding dropwise 800.3 parts by weight of an ethyl acetate solution containing 29.6% of peracetic acid and 0.40 g of potassium pyrophosphate while blowing air.

The reaction was carried out at 40° C. for 4 hours, and further aging was carried out for 4 hours. After the completion of the reaction, a reaction crude solution was washed with water thrice. Subsequently, low-boiling-point ingredients were removed with an evaporator to obtain 351.6 parts by weight of an epoxymethacrylate. Delta values of $^1$H-NMR related to the epoxymethacrylate are shown below.
Delta (ppm)
Vicinity of 1.3–1.4 (6.0H): proton in —CH$_3$ bonded to epoxy group
Vicinity of 1.95 (3.0H): proton in —CH$_3$ of methacrylic group
Vicinity of 3.0–3.1 (1.0H): proton in —CH of epoxy group
Vicinity of 4.1 (1.0H): proton in —CH$_2$— group bonded to oxygen atom of ester bond
Vicinity of 4.4 (1.0H): proton in —CH$_2$— group bonded to oxygen atom of ester bond
Vicinity of 5.6 (1.0H): one proton in CH$_2$= in methacrylic group
Vicinity of 6.1 (1.0H): one proton in CH$_2$= in methacrylic group By the values, it is identified that 3-methyl-2,3-epoxy butylmethacrylate was obtained which is a desired product having the following chemical formula.

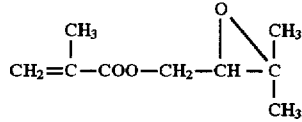

EXAMPLE 12

<Preparation of an epoxymethacrylate represented by the general formula (1-2)>

A jacketed-reaction vessel equipped with a reflux condenser, thermometer, and an agitator having blades was charged with 315 parts by weight of the methacrylate having an alkenyl group represented by the following chemical formula

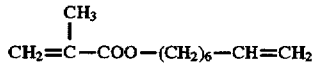

and 0.32 part by weight of hydroquinone monomethylether, followed by carrying out epoxidation reaction by adding dropwise 495.2 parts by weight of an ethyl acetate solution containing 29.6% of peracetic acid and 0.33 part by weight of potassium pyrophosphate while blowing air.

The reaction was carried out at 40° C. for 4 hours, and further aging was carried out for 6 hours. After the completion of the reaction, a reaction crude solution was washed with water thrice. Subsequently, low-boiling-point ingredients were removed with an evaporator to obtain 311.0 parts by weight of an epoxymethacrylate. Delta values of $^1$H-NMR related to the epoxymethacrylate are shown below.
Delta (ppm)
Vicinity of 1.2–1.8 (10H): proton in —CH$_2$— group
Vicinity of 1.95 (3.0H): proton in —CH$_3$ of methacrylic group
Vicinity of 2.4–2.5 (1.0H): one proton in —CH$_2$ of epoxy group
Vicinity of 2.7–2.8 (1.0H): one proton in —CH$_2$— of epoxy group
Vicinity of 2.9 (1.0H): proton in —CH— of epoxy group
Vicinity of 4.1–4.2 (2.1H): proton in —CH$_2$— group bonded to oxygen atom of ester bond
Vicinity of 5.5–5.6 (1.0H): one proton in CH2= in methacrylic group
Vicinity of 6.1 (1.0H): one proton in CH$_2$= in methacrylic group By the values, it is identified that 7.8-epoxy octylmethacrylate was obtained which is a desired product having the following chemical formula.

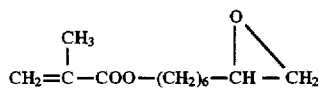

EXAMPLE 13

<Preparation of an epoxymethacrylate represented by the general formula (1-2)>

A jacketed-reaction vessel equipped with a reflux condenser, thermometer, and an agitator having blades was charged with 400 parts by weight of the methacrylate having an alkenyl group represented by the following chemical formula

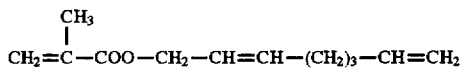

and 0.4 part by weight of hydroquinone monomethylether, followed by carrying out epoxidation reaction by adding dropwise 1270.5 parts by weight of an ethyl acetate solution containing 29.6% of peracetic acid and 0.64 part by weight of potassium pyrophosphate while blowing air.

The reaction was carried out at 40° C. for 4 hours, and further aging was carried out for 6 hours. After the completion of the reaction, a reaction crude solution was washed with water thrice. Subsequently, low-boiling-point ingredients were removed with an evaporator to obtain 420.3 parts by weight of an epoxymethacrylate.

It was identified that the epoxymethacrylate has the following chemical formula.

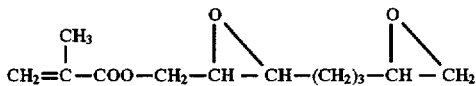

EXAMPLE 14

<Preparation of an epoxyacrylate represented by the general formula (1-2)>

A jacketed-reaction vessel equipped with a reflux condenser, thermometer, and an agitator having blades was charged with 250 parts by weight of the acrylate having an alkenyl group represented by the following chemical formula

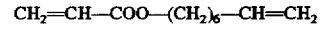

and 0.25 part by weight of hydroquinone monomethylether, followed by carrying out epoxidation reaction by adding dropwise 423.2 parts by weight of an ethyl acetate solution containing 29.6% of peracetic acid and 0.21 part by weight of potassium pyrophosphate while blowing air.

The reaction was carried out at 40° C. for 4 hours, and further aging was carried out for 6 hours. After the completion of the reaction, a reaction crude solution was washed with water thrice. Subsequently, low-boiling-point ingredients were removed with an evaporator to obtain 245.0 parts by weight of an epoxyacrylate.

It was identified that the epoxyacrylate has the following chemical formula.

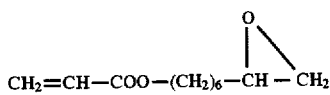

EXAMPLE 15

<Preparation of an epoxyacrylate represented by the general formula (1-2)>

A jacketed-reaction vessel equipped with a reflux condenser, thermometer, and an agitator having blades was charged with 400 parts by weight of the methacrylate having an alkenyl group represented by the following chemical formula

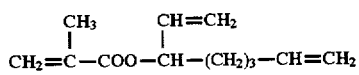

and 0.4 part by weight of hydroquinone monomethylether, followed by carrying out epoxidation reaction by adding dropwise 1270.5 parts by weight of an ethyl acetate solution containing 29.6% of peracetic acid and 0.64 part by weight of potassium pyrophosphate while blowing air.

The reaction was carried out at 40° C. for 4.5 hours, and further aging was carried out for 4 hours. After the completion of the reaction, a reaction crude solution was washed with water thrice. Subsequently, low-boiling-point ingredients were removed with an evaporator to obtain 389 parts by weight of an epoxyacrylate.

It was identified that the epoxyacrylate has the following chemical formula.

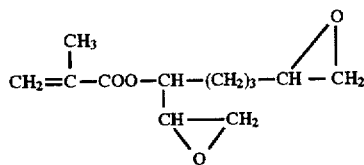

EXAMPLE 16

<Preparation of an epoxyacrylate represented by the general formula (1-2)>

A jacketed-reaction vessel equipped with a reflux condenser, thermometer, and an agitator having blades was charged with 400 parts by weight of the acrylate having an alkenyl group represented by the following chemical formula

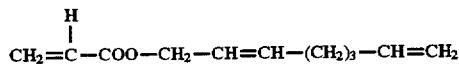

and 0.4 part by weight of hydroquinone monomethylether, followed by carrying out epoxidation reaction by adding dropwise 1369.4 parts by weight of an ethyl acetate solution containing 29.6% of peracetic acid and 0.68 part by weight of potassium pyrophosphate while blowing air.

The reaction was carried out at 40° C. for 4.5 hours, and further aging was carried out for 3 hours. After the completion of the reaction, a reaction crude solution was washed with water thrice. Subsequently, low-boiling-point ingredients were removed with an evaporator to obtain 428 parts by weight of an epoxyacrylate.

It was identified that the epoxyacrylate has the following chemical formula.

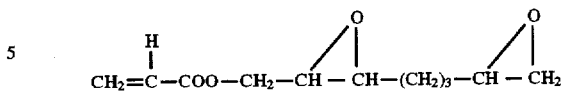

EXAMPLE 17

<Measurements of a reactivity relating to the epoxy (meth)acrylates obtained in Examples 9–12 and 14, and conventional epoxymethacrylates>

A flask was charged with 0.025 mol of the respective epoxy(meth)acrylates obtained in Examples 9–12 and 14, and 3,4-epoxycyclohexylmethylmethacrylate, beta-methylglycidyl methacrylate, and glycidyl methacrylate which are conventional epoxy methacrylates, and 50 g of dichloroethane while stirring, followed by controlling the temperature at 20° C. after adding 0.8 g of methanol. Subsequently, a dichloroethane solution containing 24 mg of $BF_3(OC_2H_5)_2$ was added to measure the reactivity of epoxy group.

Measurements were carried out by monitoring oxirane oxygen.

Results are shown in FIG. 1. The curves (a), (b), (c), (d), and (e) exhibit the respective reactivity of the epoxymethacrylates obtained in the Examples 9–12 and 14, respectively.

The curves (f), (g), and (h) exhibit the respective reactivity of 3,4-epoxycyclohexylmethylmethacrylate, beta-methylglycidyl methacrylate, and glycidyl methacrylate which are conventional epoxy methacrylates.

EXAMPLE 18

<Preparation of a methacrylic resin having alkenyl group-containing side chains represented by the general formula (1-3)>

A separable flask equipped with an agitator, thermometer, a reflux condenser, a dropwise funnel, a tube for blowing air was charged with 50 parts by weight of dioxane and 3 parts by weight of Perbutyl O (manufactured by Nihon Yushi, Ltd.) as an initiator, followed by adding 43 parts by weight of the methacrylate having an alkenyl group represented by the following chemical formula

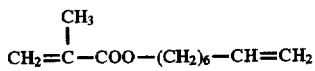

The dropwise funnel was charged with 50 parts by weight of dioxane and 4 parts by weight of Perbutyl O. The mixture composed of dioxane and perbutyl O was added dropwise into the flask at 80° C. over approximately 2 hours, followed by aging over 3 hours to obtain a reaction liquid containing a methacrylate resin.

The reaction liquid was analyzed by an internal standard method of gas chromatography to identify less than 1% of the residual methacrylate having an alkenyl group. It was identified that the reaction liquid contains 30% of the methacrylate resin having a number average molecular weight of 18,000.

EXAMPLE 19

<Preparation of a methacrylic resin having alkenyl groupcontaining side chains represented by the general formula (1-3)>

A separable flask equipped with an agitator, thermometer, a reflux condenser, a dropwise funnel, a tube for blowing air was charged with 50 parts by weight of dioxane and 3 parts by weight of Perbutyl O (manufactured by Nihon Yushi, Ltd.) as an initiator, followed by adding 54 parts by weight of methylmethacrylate, 6 parts by weight of methacrylic acid, and 40 parts by weight of the methacrylate having an alkenyl group represented by the following chemical formula

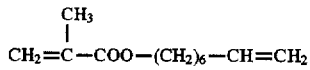

The dropwise funnel was charged with 50 parts by weight of dioxane and 4 parts by weight of Perbutyl O. The mixture composed of dioxane and perbutyl O was added dropwise into the flask at 80° C. over approximately 2 hours, followed by aging over 3 hours to obtain a reaction liquid containing a methacrylic resin.

The reaction liquid was analyzed by an internal standard method of gas chromatography to identify less than 1% of the residual methacrylate having an alkenyl group. It was identified that the reaction liquid contains 50% of the methacrylate resin having a number average molecular weight of 20,000 and an acid value of 18.5 mgKOH/g.

EXAMPLE 20

<Preparation of a methacrylic resin having alkenyl group-containing side chains represented by the general formula (1-3)>

A separable flask equipped with an agitator, thermometer, a reflux condenser, a dropwise funnel, a tube for blowing air was charged with 50 parts by weight of dioxane and 3 parts by weight of Perbutyl O (manufactured by Nihon Yushi, Ltd.) as an initiator, followed by adding 54 parts by weight of methylmethacrylate, 6 parts by weight of methacrylic acid, and 40 parts by weight of the methacrylate having an alkenyl group represented by the following chemical formula

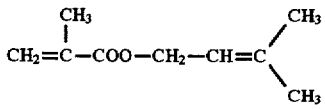

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction liquid containing a methacrylic resin.

The reaction liquid was analyzed by an internal standard method of gas chromatography to identify less than 1% of the residual methacrylate having an alkenyl group. It was identified that the reaction liquid contains 50% of the methacrylate resin having a number average molecular weight of 17,000 and an acid value of 18.7 mgKOH/g.

EXAMPLE 21

<Preparation of a methacrylic resin having alkenyl group-containing side chains represented by the general formula (1-3)>

A separable flask equipped with an agitator, thermometer, a reflux condenser, a dropwise funnel, a tube for blowing air was charged with 50 parts by weight of dioxane and 3 parts by weight of Perbutyl O (manufactured by Nihon Yushi, Ltd.) as an initiator, followed by adding 54 parts by weight of methylmethacrylate, 6 parts by weight of methacrylic acid, and 40 parts by weight of the methacrylate having an alkenyl group represented by the following chemical formula

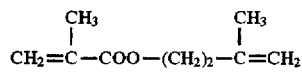

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction liquid containing a methacrylic resin.

The reaction liquid was analyzed by an internal standard method of gas chromatography to identify less than 1% of the residual methacrylate having an alkenyl group. It was identified that the reaction liquid contains 50% of the methacrylate resin having a number average molecular weight of 17,000 and an acid value of 18.7 mgKOH/g.

EXAMPLE 22

<Preparation of a methacrylic resin having alkenyl group-containing side chains represented by the general formula (1-3)>

A separable flask equipped with an agitator, thermometer, a reflux condenser, a dropwise funnel, a tube for blowing air was charged with 50 parts by weight of dioxane and 3 parts by weight of Perbutyl O (manufactured by Nihon Yushi, Ltd.) as an initiator, followed by adding 54 parts by weight of methylmethacrylate, 6 parts by weight of methacrylic acid, and 40 parts by weight of the methacrylate having an alkenyl group represented by the following chemical formula

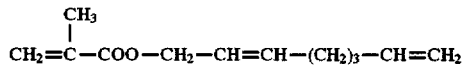

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction liquid containing a methacrylic resin.

The reaction liquid was analyzed by an internal standard method of gas chromatgraphy to identify less than 1% of the residual methacrylate having an alkenyl group. It was identified that the reaction liquid contains 50% of the methacrylate resin having a number average molecular weight of 17,000 and an acid value of 19.1 mgKOH/g.

EXAMPLE 23

<Preparation of a methacrylic resin having alkenyl group-containing side chains represented by the general formula (1-3)>

A separable flask equipped with an agitator, thermometer, a reflux condenser, a dropwise funnel, a tube for blowing air was charged with 50 parts by weight of dioxane and 3 parts by weight of Perbutyl O (manufactured by Nihon Yushi, Ltd.) as an initiator, followed by adding 54 parts by weight of methylmethacrylate, 5 parts by weight of n-butyl acrylate, 5 parts by weight of 2-hydroxyethyl methacrylate, 3 parts by weight of methacrylic acid, 5 parts by weight of a caprolactone-modifiedhydroxyethyl methacrylate having average molecular weight of 244 (PCL-FM1 manufactured by Daicel Chemical Industries, Ltd.), and 10 parts by weight of the methacrylate having an alkenyl group represented by the following chemical formula

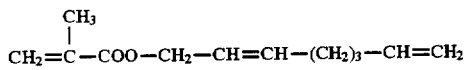

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction liquid containing a methacrylic resin. The reaction liquid was analyzed by an internal standard method of gas chromatgraphy to identify less than 1% of the residual methacrylate having an alkenyl group. It was identified that the reaction liquid contains 38% of the methacrylate resin having a number average molecular weight of 20,000 and an acid value of 12.3 mgKOH/g, and a hydroxyl value of 20.1 mgKOH/g.

EXAMPLE 24

<Preparation of a methacrylic resin having alkenyl group-containing side chains represented by the general formula (1-3)>

A separable flask equipped with an agitator, thermometer, a reflux condenser, a dropwise funnel, a tube for blowing air was charged with 50 parts by weight of xylene and 3 parts by weight of Perbutyl O (manufactured by Nihon Yushi, Ltd.) as an initiator, followed by adding 20 parts by weight of methylmethacrylate, 5 parts by weight of acrylic acid, 10 parts by weight of styrene, 5 parts by weight of 2-hydroxyethyl methacrylate, 2 parts by weight of methacrylic acid, 5 parts by weight of a caprolactone-modified hydroxyethyl methacrylate (PCL FM-1 manufactured by Daicel Chemical Industries, Ltd.), and 10 parts by weight of the methacrylate having an alkenyl group represented by the following chemical formula

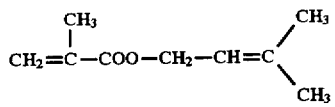

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction liquid containing a methacrylic resin.

The reaction liquid was analyzed by an internal standard method of gas chromatgraphy to identify less than 1% of the residual methacrylate having an alkenyl group. It was identified that the reaction liquid contains 37% of the methacrylate resin having a number average molecular weight of 17,000, an acid value of 8.0 mgKOH/g, and a hydroxyl value of 20.5 mgKOH/g.

EXAMPLE 25

<Preparation of a (meth)acrylic resin having epoxy group-containing side chains represented by the general formula (1-4)>

A separable flask equipped with an agitator, thermometer, a reflux condenser, a dropwise funnel, a tube for blowing nitrogen was charged with 50 parts by weight of dioxane and 3 parts by weight of Perbutyl O (manufactured by Nihon Yushi, Ltd.) as an initiator, followed by adding 43 parts by weight of the epoxymethacrylate represented by the following chemical formula

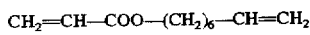

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction liquid containing a methacrylic resin having epoxy group-containing side chains.

The reaction liquid was analyzed by an internal standard method of gas chromatgraphy to identify less than 1% of the residual epoxymethacrylate. It was identified that the reaction liquid contains 30% of the methacrylic resin having epoxy group-containing side chains having a number average molecular weight of 20,000.

EXAMPLE 26

<Preparation of a (meth)acrylic resin having epoxy group-containing side chains represented by the general formula (1-4)>

A 1-liter glass-made reaction flask equipped with an agitator, thermometer, a Dimroth condenser, a dropwise funnel, a tube for blowing nitrogen was charged with 50 parts by weight of dioxane and 3 parts by weight of Perbutyl O (manufactured by Nihon Yushi, Ltd.) as an initiator, followed by adding 54 parts by weight of methylmethacrylate, 6 parts of methacrylic acid, 40 parts by weight of the epoxymethacrylate represented by the following chemical formula

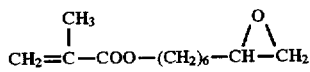

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction composition containing a methacrylic resin having epoxy group-containing side chains.

The reaction composition was obtained as a solution containing 50% of the methacrylic resin having epoxy group-containing side chains having a number average molecular weight of 20,000, oxirane oxygen concentration of 1.3%, and an acid value of 18.5 mgKOH/g.

EXAMPLE 27

<Preparation of a (meth)acrylic resin having epoxy group-containing side chains represented by the general formula (1-4)>

A 1-liter glass-made reaction flask equipped with an agitator, thermometer, a Dimroth condenser, a dropwise funnel, a tube for blowing nitrogen was charged with 50 parts by weight of dioxane and 3 parts by weight of Perbutyl O (manufactured by Nihon Yushi, Ltd.) as an initiator, followed by adding 54 parts by weight of methylmethacrylate, 6 parts of methacrylic acid, 40 parts by weight of the epoxymethacrylate represented by the following chemical formula

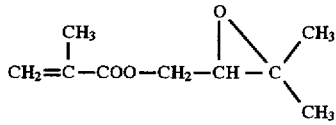

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction composition containing a methacrylic resin having epoxy group-containing side chains.

The reaction composition was as a solution containing 48% of the methacrylic resin having epoxy group-containing side chains having a number average molecular weight of 19,000, oxirane oxygen concentration of 1.6%, and an acid value of 17.5 mgKOH/g.

EXAMPLE 28

<Preparation of a (meth)acrylic resin having epoxy group-containing side chains represented by the general formula (1-4)>

A 1-liter glass-made reaction flask equipped with an agitator, thermometer, a Dimroth condenser, a dropwise funnel, a tube for blowing nitrogen was charged with 50 parts by weight of dioxane and 3 parts by weight of Perbutyl O (manufactured by Nihon Yushi, Ltd.) as an initiator, followed by adding 54 parts by weight of methylmethacrylate, 6 parts of methacrylic acid, 40 parts by weight of the epoxymethacrylate represented by the following chemical formula

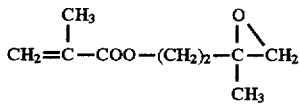

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction composition containing a methacrylic resin having epoxy group-containing side chains.

The reaction composition was obtained as a solution containing 48% of the methacrylic resin having epoxy group-containing side chains having a number average molecular weight of 19,000, oxirane oxygen concentration of 1.6%, and an acid value of 17.5 mgKOH/g.

EXAMPLE 29

<Preparation of a (meth)acrylic resin having epoxy group-containing side chains represented by the general 'formula (1-4)>

A 1-liter glass-made reaction flask equipped with an agitator, thermometer, a Dimroth condenser, a dropwise funnel, a tube for blowing nitrogen was charged with 50 parts by weight of dioxane and 3 parts by weight of Perbutyl O (manufactured by Nihon Yushi, Ltd.) as an initiator, followed by adding 35 parts by weight of methylmethacrylate, 5 parts of n-butyl acrylate, 5 parts by weight of the 2-hydroxyethylmethacrylate, 3 parts by weight of methacrylic acid, 15 parts by weight of the epoxymethacrylate represented by the following chemical formula

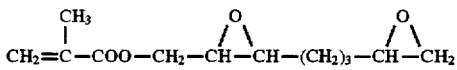

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction composition.

The reaction composition was obtained as a solution containing 39.5% of a methacrylic resin having epoxy group-containing side chains which has a number average molecular weight of 5,000, oxirane oxygen concentration of 1.1%, an acid value of 11.0 mgKOH/g, and a hydroxyl value of 13 mgKOH/g.

EXAMPLE 30

<Preparation of a (meth)acrylic resin having epoxy group-containing side chains represented by the general formula (1-4)>

A 1-liter glass-made reaction flask equipped with an agitator, thermometer, a Dimroth condenser, a dropwise funnel, a tube for blowing nitrogen was charged with 50 parts by weight of dioxane and 3 parts by weight of Perbutyl O (manufactured by Nihon Yushi, Ltd.) as an initiator, followed by adding 30 parts by weight of methylmethacrylate, 5 parts of n-butyl acrylate, 5 parts by weight of the 2-hydroxyethylmethacrylate, 3 parts by weight of methacrylic acid, 5 parts by weight of a caprolactone-modified hydroxyethyl methacrylate (PCL FM-1 manufactured by Daicel Chemical Industries, Ltd.), and 10 parts by weight of the epoxymethacrylate represented by the following chemical formula

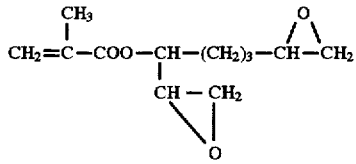

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction composition containing a methacrylic resin having epoxy group-containing side chains.

The reaction composition was obtained as a solution containing 40.2% of the methacrylic resin having epoxy group-containing side chains having a number average molecular weight of 5,500, oxirane oxygen concentration of 1.2%, an acid value of 12.0 mgKOH/g, and a hydroxyl value of 12.5 mgKOH/g.

EXAMPLE 31

<Preparation of a (meth)acrylic resin having epoxy group-containing side chains represented by the general formula (1-4)>

A 1-liter glass-made reaction flask equipped with an agitator, thermometer, a Dimroth condenser, a dropwise funnel, a tube for blowing nitrogen was charged with 50 parts by weight of dioxane and 3 parts by weight of Perbutyl O (manufactured by Nihon Yushi, Ltd.) as an initiator, followed by adding 30 parts by weight of methylmethacrylate, 5 parts of n-butyl acrylate, 5 parts by weight of the 2-hydroxyethylmethacrylate, 3 parts by weight of methacrylic acid, 5 parts by weight of a caprolactone-modified hydroxyethyl methacrylate (PCL FM-1 manufactured by Daicel Chemical Industries, Ltd.), and 10 parts by weight of the epoxymethacrylate represented by the following chemical formula

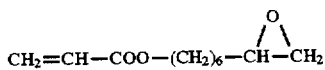

The dropwise funnel was charged with 50 parts by weight of xylene and 4 parts by weight of Perbutyl O. The mixture composed of dioxane and Perbutyl O was added dropwise into the flask at 80° C. over approximately 2 hours, followed by aging over 3 hours to obtain a reaction composition containing a methacrylic resin having epoxy group-containing side chains.

The reaction composition was obtained as a solution containing 39% of the methacrylic resin having epoxy group-containing side chains having a number average molecular weight of 7,000, oxirane oxygen concentration of 0.40%, an acid value of 12.0 mgKOH/g, and a hydroxyl value of 18.0 mgKOH/g.

EXAMPLE 32

<Preparation of a (meth)acrylic resin having epoxy group-containing side chains represented by the general formula (1-4)>

A 1-liter glass-made reaction flask equipped with an agitator, thermometer, a Dimroth condenser, a dropwise funnel, a tube for blowing nitrogen was charged with 50 parts by weight of dioxane and 3 parts by weight of Perbutyl O (manufactured by Nihon Yushi, Ltd.) as an initiator, followed by adding 30 parts by weight of methylmethacrylate, 5 parts of n-butyl acrylate, 5 parts by weight of the 2-hydroxyethylmethacrylate, 3 parts by weight of methacrylic acid, 5 parts by weight of a caprolactone-modified hydroxyethyl methacrylate (PCL FM-1 manufactured by Daicel Chemical Industries, Ltd.), and 10 parts by weight of the epoxymethacrylate represented by the following chemical formula

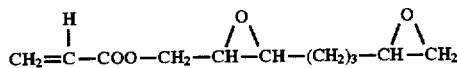

The dropwise funnel was charged with 50 parts by weight of xylene and 4 parts by weight of Perbutyl O. The mixture composed of dioxane and Perbutyl O was added dropwise into the flask at 80° C. over approximately 2 hours, followed by aging over 3 hours to obtain a reaction composition containing a methacrylic resin having epoxy group-containing side chains.

The reaction composition was obtained as a solution containing 40% of the methacrylic resin having epoxy group-containing side chains having a number average molecular weight of 4,900, oxirane oxygen concentration of 0.89%, an acid value of 11.9 mgKOH/g, and a hydroxyl value of 19.0 mgKOH/g.

EXAMPLE 33

<Preparation of a (meth)acrylic resin having epoxy group-containing side chains represented by the general formula (1-4)>

A 1-liter glass-made reaction flask equipped with an agitator, thermometer, a Dimroth condenser, a dropwise funnel, a tube for blowing nitrogen was charged with 50 parts by weight of xylene and 3 parts by weight of Perbutyl O (manufactured by Nihon Yushi, Ltd.) as an initiator, followed by adding 20 parts by weight of methylmethacrylate, 5 parts of n-butyl acrylate, 10 parts by weight of styrene, 5 parts by weight of the 2-hydroxyethylmethacrylate, 2 parts by weight of methacrylic acid, 5 parts by weight of a caprolactone-modified hydroxyethyl methacrylate (PCL FM-1 manufactured by Daicel Chemical Industries, Ltd.), and 10 parts by weight of the epoxymethacrylate represented by the following chemical formula

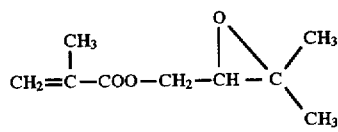

The dropwise funnel was charged with 50 parts by weight of xylene and 4 parts by weight of Perbutyl O. The mixture composed of dioxane and Perbutyl O was added dropwise into the flask at 80° C. over approximately 3 hours, followed by aging over 3 hours to obtain a reaction composition containing a methacrylic resin having epoxy group-containing side chains.

The reaction composition was obtained as a solution containing 38.1% of the methacrylic resin having epoxy group-containing side chains having a number average molecular weight of 5,800, oxirane oxygen concentration of 0.52%, an acid value of 8.0 mgKOH/g, and a hydroxyl value of 19.0 mgKOH/g.

EXAMPLE 34

<Preparation of a (meth)acrylic resin having epoxy group-containing side chains represented by the general formula (1-4)>

A 1-liter glass-made reaction flask equipped with an agitator, thermometer, a Dimroth condenser, a dropwise funnel, a tube for blowing nitrogen was charged with 50 parts by weight of xylene and 3 parts by weight of Perbutyl O (manufactured by Nihon Yushi, Ltd.) as an initiator, followed by adding 20 parts by weight of methylmethacrylate, 5 parts of n-butyl acrylate, 10 parts by weight of styrene, 5 parts by weight of the 2-hydroxyethylmethacrylate, 2 parts by weight of methacrylic acid, 5 parts by weight of a caprolactone-modified hydroxyethyl methacrylate (PCL FM-1 manufactured by Daicel Chemical Industries, Ltd.), and 10 parts by weight of the epoxymethacrylate represented by the following chemical formula

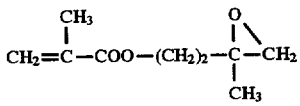

The dropwise funnel was charged with 50 parts by weight of xylene and 4 parts by weight of Perbutyl O. The mixture composed of dioxane and Perbutyl O was added dropwise into the flask at 80° C. over approximately 3 hours, followed by aging over 3 hours to obtain a reaction composition containing a methacrylic resin having epoxy group-containing side chains.

The reaction composition was obtained as a solution containing 37.9% of the methacrylic resin having epoxy group-containing side chains having a number average molecular weight of 6,200, oxirane oxygen concentration of 0.48%, an acid value of 7.8 mgKOH/g, and a hydroxyl value of 20.2 mgKOH/g.

EXAMPLE 35

<Preparation of a (meth)acrylic resin having epoxy group-containing side chains represented by the general formula (1-4)>

A 1-liter glass-made reaction flask equipped with an agitator, thermometer, a Dimroth condenser, a dropwise funnel, a tube for blowing nitrogen was charged with 50 parts by weight of xylene and 3 parts by weight of Perbutyl O (manufactured by Nihon Yushi, Ltd.) as an initiator, followed by adding 54 parts by weight of methylmethacrylate, 6 parts by weight of methacrylic acid, and 40 parts by weight of the epoxymethacrylate represented by the following chemical formula

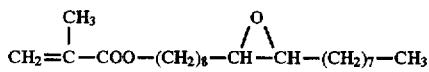

The dropwise funnel was charged with 50 parts by weight of xylene and 4 parts by weight of Perbutyl O. The mixture composed of dioxane and Perbutyl O was added dropwise into the flask at 80° C. over approximately 2 hours, followed by aging over 4 hours to obtain a reaction composition containing a methacrylic resin having epoxy group-containing side chains.

The reaction composition was obtained as a solution containing 49% of the methacrylic resin having epoxy group-containing side chains having a number average molecular weight of 6,500, oxirane oxygen concentration of 0.69%, an acid value of 18.7 mgKOH/g.

EXAMPLE 36

<Preparation of a (meth)acrylic resin having epoxy group-containing side chains represented by the general formula (1-4)>

A 1-liter glass-made reaction flask equipped with an agitator, thermometer, a Dimroth condenser, a dropwise funnel, a tube for blowing nitrogen was charged with 50 parts by weight of dioxane and 3 parts by weight of Perbutyl O (manufactured by Nihon Yushi, Ltd.) as an initiator, followed by adding 54 parts by weight of methylmethacrylate, 6 parts by weight of methacrylic acid, and 40 parts by weight of the epoxyacrylate represented by the following chemical formula

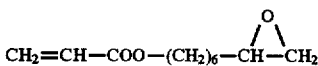

The dropwise funnel was charged with 50 parts by weight of dioxane and 4 parts by weight of Perbutyl O. The mixture composed of dioxane and Perbutyl O was added dropwise into the flask at 80° C. over approximately 2 hours, followed by aging over 3 hours to obtain a reaction composition containing an acrylic resin having epoxy group-containing side chains.

The reaction composition was obtained as a solution containing 50% of the methacrylic resin having epoxy group-containing side chains having a number average molecular weight of 21,000, oxirane oxygen concentration of 1.4%, an acid value of 18.5 mgKOH/g.

EXAMPLE 37

<Preparation of thermosetting resin compositions>

Preparation Example 1

<Preparation of a (meth)acrylic resin having epoxy group-containing side chains represented by the general formula (1-4)>

A 2-liter glass-made reaction flask equipped with an agitator, thermometer, a Dimroth condenser, a dropwise funnel, a tube for blowing nitrogen was charged with 150 parts by weight of xylene, 150 parts by weight of propyleneglycol monomethylether acetate, 3 parts by weight of Perbutyl O (manufactured by Nihon Yushi, Ltd.), 200 parts by weight of methylmethacrylate, 85 parts of methacrylic acid, 100 parts by weight of styrene, 500 parts by weight of the 2-ethylhexyl-methacrylate, 50 parts by weight of a caprolactone-modified hydroxyethyl methacrylate (PCL FM-1 manufactured by Daicel Chemical Industries, Ltd.), and 200 parts by weight of the epoxymethacrylate represented by the following chemical formula

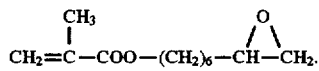

The dropwise funnel was charged with 150 parts by weight of xylene 150 parts by weight of propyleneglycol monomethylether acetate, 4 parts by weight of Perbutyl O. The mixture composed of dioxane and Perbutyl O was added dropwise into the flask at 80° C. over approximately 2 hours, followed by aging over 3 hours to obtain a reaction composition containing a methacrylic resin having epoxy group-containing side chains.

The reaction composition was obtained as a solution containing 53% of the methacrylic resin having epoxy group-containing side chains having a number average molecular weight of 6,500, oxirane oxygen concentration of 2.2%, and an acid value of 81 mgKOH/g.

The methacrylic resin was designated as MR-1.

Preparation Examples 2-7

<Preparation of a (meth)acrylic resin having epoxy group-containing side chains represented by the general formula (1-4)>

The same procedures were repeated as described in Preparation Example 1, except that components were changed as shown in Table 1.

TABLE 1

| | Preparation Example | | | | | |
|---|---|---|---|---|---|---|
| | 2 | 3 | 4 | 5 | 6 | 7 |
| Mixing ratio(parts by weight) | | | | | | |
| xylene | 150 | 150 | 150 | 150 | 150 | 150 |
| PMEA | 150 | 150 | | | | |
| BA | | | 150 | 150 | 150 | 150 |
| Perbutyl O | 3 | 3 | 3 | 3 | 3 | 3 |
| 2-HEMA | | | | | | 250 |
| MMA | 100 | 100 | 200 | 200 | 200 | 200 |
| MA | 105 | 105 | | | | |
| styrene | 150 | 150 | 100 | 100 | 100 | |
| g-TMPMA | | | 203 | 203 | 250 | 100 |
| 2-EHMA | | | | | | |

TABLE 1-continued

| | Preparation Example | | | | | |
|---|---|---|---|---|---|---|
| | 2 | 3 | 4 | 5 | 6 | 7 |
| n-BMA | 50 | 50 | | | | 100 |
| PCL FM-1 | 50 | 50 | 100 | 100 | 100 | 100 |
| EM | (2) | (3) | (4) | (5) | (6) | (7) |
| | 200 | 200 | 150 | 150 | 200 | 200 |
| Mixing ratio in Dropwise funnel (parts by weight) | | | | | | |
| xylene | 150 | 150 | 150 | 150 | 150 | 150 |
| PMEA | 150 | 150 | | | | |
| BA | | | 150 | 150 | 150 | 150 |
| Perbutyl O | 4 | 4 | 4 | 4 | 4 | 4 |
| Temperature (°C.) | 80 | 80 | 80 | 80 | 80 | 80 |
| Dropwise addition time (approx./hour) | 2 | 2 | 2 | 2 | 2 | 2 |
| Aging time (hour) | 3 | 3 | 3 | 3 | 3 | 3 |
| Solid content (%) | 52 | 50 | 47 | 50 | 58 | 60 |
| NMW | 6,500 | 6500 | 7500 | 7500 | 8200 | 9500 |
| OX (%) | 2.7 | 2.8 | 3.4 | 3.4 | 1.9 | 1.6 |
| AV (mgKOH/g) | 103 | 105 | | | | |

Abbreviations in the Table 1 and the epoxymethacrylates (2) to (7) employed in the Preparation Examples 2 to 7 are described below.

PMEA: propyleneglycol monomethylether acetate

BA: butyl acetate

MMA: methylmethacrylate

MA: methacrylic acid

2-EHMA: 2-ethylhexylmethacrylate g-TMPMA: gamma-trimethoxysilylpropylmethacrylate PCL FM-1: a caprolactone-modified hydroxyethyl methacrylate manufactured by Daicel Chemical Industries, Ltd.

EM: epoxymethacrylate represented by the following respective formula
  (2) the epoxymethacrylate obtained in Example 10
  (3) the epoxymethacrylate obtained in Example 11
  (4) the epoxyacrylate obtained in Example 16
  (5) the epoxymethacrylate obtained in Example 15
  (6) the epoxymethacrylate obtained in Example 12
  (7) the epoxymethacrylate obtained in Example 12 n-BMA: n-butylmethacrylate

NMW: a number average molecular weight

OX: oxirane oxygen concentration

AV: an acid value

Application Example 1

100 parts by weight of the respective epoxymethacrylates prepared in Preparation Examples 1 and 2, and 1 part by weight of tetrabutylammonium bromide were mixed while diluting with 1/1 mixed solvent composed of xylene and butyl acetate to prepare clear coating compositions. The respective compositions were coated on a plate (manufactured by Nihon Test Panel, Ltd., hereinafter, the same) for electrodeposition coating with a Barcoater, followed by baking at 140°C. for 30 minutes to prepare Coating Layers 1 and 2.

Application Example 2

100 parts by weight of the epoxymethacrylate prepared in Preparation Example 3 and 1 part by weight of tetraphenylphosphonium chloride were mixed while diluting with 1/1 mixed solvent composed of xylene and butyl acetate to prepare a clear coating composition. The composition was coated on a plate for electrodeposition coating with a Barcoater, followed by baking at 140° C. for 30 minutes to prepare Coating Layer 3.

Application Example 3

100 parts by weight of the epoxymethacrylate prepared in Preparation Example 4 and 2 part by weight of tris(n-propylacetoacetate)aluminum were mixed while diluting with 20 parts by weight of a purified 3,4-epoxycyclohexyl-3,4-cyclohexanecarboxylate (Celloxide 2021P manufactured by Daicel Chemical Industries, Ltd.) to prepare a clear coating composition. The composition was coated on a plate for electrodeposition coating with a Barcoater, followed by baking at 85° C. for 30 minutes to prepare Coating Layer 4.

Application Example 4

100 parts by weight of the epoxymethacrylate prepared in Preparation Example 5 and 2 part by weight of tris(n-propylacetoacetate) zirconium were mixed while diluting with 20 parts by weight of a purified 3,4-epoxycyclohexyl-3,4-cyclohexanecarboxylate (Celloxide 2021P manufactured by Daicel Chemical Industries, Ltd.) to prepare a clear coating composition. The composition was coated on a plate for electrodeposition coating with a barcoater, followed by baking at 85° C. for 30 minutes to prepare Coating Layer 5.

Application Example 5

100 parts by weight of the epoxymethacrylate prepared in Preparation Example 6 and 2 part by weight of tris (acetylacetonate)aluminum were mixed while diluting with 20 parts by weight of a purified 3,4-epoxycyclohexyl-3,4-cyclohexanecarboxylate (Celloxide 2021P manufactured by Daicel Chemical Industries, Ltd.) to prepare a clear coating composition. The composition was coated on a plate for electrodeposition coating with a barcoater, followed by baking at 85° C. for 30 minutes to prepare Coating Layer 6.

Application Example 6

100 parts by weight of the epoxymethacrylate prepared in Preparation Example 7 and 0.1 part by weight of phosphoric acid were mixed while diluting with 1/1 solution composed of xylene and butyl acetate to prepare a clear coating composition. The composition was coated on a plate for electrodeposition coating with a barcoater, followed by baking at 85° C. for 60 minutes to prepare Coating Layer 7.

Application Example 7

100 parts by weight of the epoxymethacrylate prepared in Preparation Example 7 and 2 part by weight of phosphoric acid-2-ethylhexyl were mixed while diluting with 1/1 solution composed of xylene and butyl acetate to prepare a clear coating composition. The composition was coated on a plate for electrodeposition coating with a Barcoater, followed by baking at 85° C. for 60 minutes to prepare Coating Layer 8.

Application Example 8

100 parts by weight of the epoxymethacrylate prepared in Preparation Example 7 and 0.1 part by weight of phosphoric acid were mixed while diluting with 20 parts by weight of a purified 3,4-epoxycyclohexyl-3,4-cyclohexanecarboxylate (Celloxide 2021P manufactured by Daicel Chemical Industries, Ltd.) to prepare a clear coating composition. The composition was coated on a plate for electrodeposition coating with a barcoater, followed by baking at 85° C. for 60 minutes to prepare Coating Layer 9.

<Evaluation of Coating Layer>

There were evaluated properties in relation to the Coating Layers 1 to 9 obtained in Application Examples 1 to 8. The results are shown in Table 2.

Coating Stability: Clear coating composition prepared was placed at a room temperature for 10 days, and then the presence or absence of gelation and increase of viscosity was observed.

Gel Fraction: Cured coating layer was stripped from a glass plate, and then was extracted by acetone with a Soxhlet extractor for 5 hours to weigh the residue.

Impact Strength: It was measured with a Dupon't Impact Strength tester equipped with 500 g weight.

Scratch Resistance: Cleanser (New Homing Cleanser manufactured by Kao, Ltd.) was coated on a cloth (2 cm×2 cm), and coating layer was given abrasion under the load of 500 g, and retention ratio of 20° gloss was measured after 20 cycles abrasions.

Weatherability: Irradiation (for 15 minutes) at 40° to 70° C. and cooling (for 15 minutes) was repeated for 2000 hours with a QUV testing equipment, and then deterioration degree of the coating layer was visually observed.

TABLE 2

| Coating Layer No. | 1 | 2 | 3 | 4 | 5 | 6 | 7 | 8 | 9 |
|---|---|---|---|---|---|---|---|---|---|
| Coating stability | G | G | G | G | G | G | G | G | G |
| Gel fraction (%) | 99 | 98 | 97 | 97 | 96 | 98 | 99 | 97 | 96 |
| Impact strength | 50< | 50< | 50< | 50< | 50< | 50< | 50< | 50< | 50< |
| Pencil hardness | F | F | H | H | H | H | F | F | H |
| Scratch resistance | 85 | 80 | 83 | 89 | 90 | 88 | 82 | 85 | 90 |
| Weatherability | G | G | G | G | G | G | G | G | G |

In the Table 2, abbreviation G means "good".

The thermosetting resin composition of the present invention can quickly cure at low temperatures, and can provide excellent properties.

Accordingly, it can be preferably employed for coatings, adhesives, and inks, etc. Furthermore, scratch resistance in the coating layer is excellent, and it can be exceedingly preferably employed as acid-resistible coatings or coatings having weatherability for cars and construction materials.

Example 38

<Preparation of powder coating compositions>

Synthesis Example 1

<Preparation of a (meth)acrylic resin having epoxy group-containing side chains represented by the general formula (1-4)>

80 parts by weight of the epoxymethacrylate obtained in Example 12, 20 parts by weight of methacrylic acid, and 1.5 part by weight of Perhexyl Z (manufactured by Nihon Yushi, Ltd.) were added dropwise into 120 parts by weight of xylene at 150° C. to polymerize. A methacrylic resin having a molecular weight of 2000 was obtained by removing solvents after polymerization.

The methacrylic resin was designated as A-1.

Synthesis Examples 2 to 9

The same copolymerizations were repeated as in Synthesis Example 1 except that copolymerizations were carried out in a mixing ratio of epoxy acrylates, copolymerizable monomers, initiators, and solvents and at the conditions as shown in Table 3 to obtain methacrylic resins.

Molecular weight of the epoxy acrylates obtained is also shown in Table 3.

TABLE 3

| | Synthesis Example | | | | | | | |
|---|---|---|---|---|---|---|---|---|
| | 2 | 3 | 4 | 5 | 6 | 7 | 8 | 9 |
| Mixing ratio (parts by weight) | | | | | | | | |
| EM | (2) 80 | (3) 80 | (4) 80 | (5) 80 | (6) 60 | (7) 50 | (8) 45 | (9) 80 |
| MMA | 20 | 20 | 20 | 20 | 30 | 30 | 30 | 30 |
| Perhexyl Z | 1.5 | 1.5 | 1.5 | 1.5 | 1.5 | 1.5 | 1.5 | 1.5 |
| xylene (150° C.) | 120 | 120 | 120 | 120 | 120 | 120 | 120 | 120 |
| MW | 1800 | 1700 | 2500 | 2400 | 2000 | 2200 | 2600 | 2500 |
| Designated No. of Methacrylic resin obtained | | | | | | | | |
| | A-2 | A-3 | A-4 | A-5 | A-6 | A-7 | A-8 | A-9 |

In the Table 3, respective abbreviations and the epoxymethacrylates (2) to (10) employed in the Synthesis Examples 2 to 10 are as follows.

EM: Epoxy methacrylate
 (2) the epoxymethacrylate obtained in Example 10
 (3) the epoxymethacrylate obtained in Example 11
 (4) the epoxymethacrylate obtained in Example 16
 (5) the epoxymethacrylate obtained in Example 15
 (6) the epoxymethacrylate obtained in Example 12
 (7) the epoxymethacrylate obtained in Example 12
MMA: Methyl methacrylate
GMA: Glycidyl methacrylate
ST: Styrene
MW: Molecular weight Synthesis Example 10

<Preparation of a methacrylic resin using glycidyl methacrylate>

50 parts by weight of the glycidylmethacrylate, 20 parts by weight of methacrylic acid, 20 parts by weight of styrene, and 1.5 part by weight of Perhexyl Z (manufactured by Nihon Yushi, Ltd.) were added dropwise into 120 parts by weight of xylene at 150° C. to polymerize. A methacrylic resin having a molecular weight of 2500 which is a conventional methacrylic resin was obtained by removing solvents after polymerization. The methacrylic resin was designated as A-10.

Synthesis Example 11

<Preparation of a carboxyl-terminated polyester resin>

A reaction vessel equipped with an agitator, a tube for blowing nitrogen, a tube for removing low-boiling-point ingredients was charged with 1023 parts by weight of neopentylglycol, 950 parts by weight of dimethylterephthalate, 0.5 part by weight of zinc acetate, followed by raising temperature to 220° C. over 10 hours while removing methanol.

Successively, there were charged 33 parts by weight of adipic acid, 687 parts by weight of terephthalic acid, and 1 part of dimethyltin oxide, followed by allowing to react at 180° C. for 8 hours, and raising the temperature to 240° C. over 3 hours to allow to react for 2 hours.

Successively, reaction product was allowed to cool to 180° C., followed by adding 165 parts by weight of trimellitic anhydride to obtain a carboxyl-terminated polyester resin having an acid value of 34 mgKOH/g, a molecular weight of 2800, and a softening point of 118° C.

The polyester resin was designated by A-11.

Application Example 9

There were mixed 500 parts by weight of the methacrylic resin A-1, 270 parts by weight of dodecanedicarboxylic acid, 450 parts by weight of titanium oxide, and 1 part of "Modaflow" which is a fluidity modifier (manufactured by Monsanto, Ltd.) to prepare a powder coating composition by kneading with an extruder, cooling, crushing, and classifying.

The powder coating composition was coated on a zinc-plated steel plate with an electrostatic coating machine, and then baked at 180° C. for 20 minutes to prepare coating layer for measuring properties.

Application Examples 10 to 21

The same procedures were repeated as described in Application Example 9, except that components for mixing were changed as shown in Table 4.

The powder coating composition was coated on a zinc-plated steel plate with an electrostatic coating machine, and then baked at 180° C. for 20 minutes to prepare coating layer for measuring properties.

The components for mixing are shown in Table 5.

TABLE 5

|  | Comparative Example | |
|---|---|---|
|  | 1 | 2 |
| Acrylic resin (parts by weight) | | |
| A-10 | 500 | 100 |
| Curing agent (parts by weight) | | |
| dodecanedicarboxylic acid | 202 | |
| A-11 | | 580 |
| Equivalent ratio (Epoxy/COOH) | 1.0 | 1.0 |
| pigment (titanium oxide/part by weight) | 420 | 408 |

TABLE 6-1

|  | Example | | | | | | | |
|---|---|---|---|---|---|---|---|---|
|  | 1 | 2 | 3 | 4 | 5 | 6 | 7 | 8 |
| Smoothness | ○ | ○ | ○ | ○ | ○ | ○ | ○ | ○ |
| Gloss (60°) | 94 | 91 | 92 | 95 | 93 | 92 | 91 | 92 |
| Erichsen (mm) | >7 | >7 | >7 | >7 | >7 | >7 | >7 | >7 |
| Pencil hardness | F | HB | HB | H | HB | F | HB | F |
| Impact strength (cm) | 50 | 50 | 50 | 50 | 50 | 50 | 50 | 50 |
| Clinging ability (/100) | 100 | 100 | 100 | 100 | 100 | 100 | 100 | 100 |

TABLE 4

|  | Application Example | | | | | | | | | | | |
|---|---|---|---|---|---|---|---|---|---|---|---|---|
|  | 10 | 11 | 12 | 13 | 14 | 15 | 16 | 17 | 18 | 19 | 20 | 21 |
| Acrylic resin (parts by weight) | | | | | | | | | | | | |
| A-1 | | | | | | | | | 100 | | | |
| A-2 | 500 | | | | | | | | | | | |
| A-3 | | 500 | | | | | | | | | | |
| A-4 | | | 500 | | | | | | | | | |
| A-5 | | | | 500 | | | | | | | | |
| A-6 | | | | | 500 | | 100 | | | | | |
| A-7 | | | | | | 500 | | | 100 | | | |
| A-8 | | | | | | | 500 | | | | 100 | |
| A-9 | | | | | | | | 500 | | | | |
| Curing agent (parts by weight) | | | | | | | | | | | | |
| dodecanedicarboxylic acid | 270 | 270 | 405 | 200 | 160 | 170 | 225 | 160 | | | | |
| A-11 | | | | | | | | | 620 | 465 | 485 | 655 |
| Equivalent ratio (Epoxy/COOH) | 1.0 | 1.0 | 1.0 | 1.0 | 1.0 | 1.0 | 1.0 | 1.0 | 1.0 | 1.0 | 1.0 | 1.0 |
| pigment (titanium oxide/part by weight) | 450 | 450 | 525 | 420 | 400 | 400 | 435 | 460 | 430 | 339 | 351 | 453 |

Comparative Application Examples 1 and 2

There were mixed 500 parts by weight of the methacrylic resin A-10 obtained in Synthetic Example 10, 202 parts by weight of dodecanedicarboxylic acid, 420 parts by weight of titanium oxide, and 1 part of "Modaflow" which is a fluidity modifier (manufactured by Monsanto, Ltd.) to prepare a powder coating composition by kneading with an extruder, cooling, crushing, and classifying.

TABLE 6-1-continued

|  | Example | | | | | | | |
|---|---|---|---|---|---|---|---|---|
|  | 1 | 2 | 3 | 4 | 5 | 6 | 7 | 8 |
| Solvent resistance | ○ | ○ | ○ | ○ | ○ | ○ | ○ | ○ |

TABLE 6-1-continued

| | Example | | | | | | | |
|---|---|---|---|---|---|---|---|---|
| | 1 | 2 | 3 | 4 | 5 | 6 | 7 | 8 |
| Weatherability (retention ratio % of 60° Gloss) | 90 | 88 | 87 | 90 | 90 | 88 | 89 | 90 |

TABLE 6-2

| | Example | | | | | Comp. Example | |
|---|---|---|---|---|---|---|---|
| | 9 | 10 | 11 | 12 | 13 | 1 | 2 |
| Smoothness | ○ | ○ | ○ | ○ | ○ | X | X |
| Gloss (60°) | 93 | 90 | 89 | 90 | 91 | — | — |
| Erichsen (mm) | >7 | >7 | >7 | >7 | >7 | >7 | >7 |
| Pencil hardness | F | F | F | HB | HB | F | F |
| Impact strength (cm) | 50 | 50 | 50 | 50 | 50 | 10 | 10 |
| Anti-strippability (/100) | 100 | 100 | 100 | 100 | 100 | 80 | 75 |
| Solvent resistance | ○ | ○ | ○ | ○ | ○ | ○ | Δ |
| Weatherability (retention ratio % of 60° Gloss) | 85 | 86 | 88 | 84 | 85 | 69 | 58 |

Properties of coating layers were measured according to the following respective standards.

(a) Smoothness: Smoothness of cured coating layer was visually measured (○: good, Δ: slightly poor, X: poor).

(b) Gloss (60°): There was measured reflection ratio (%) by an angle of incidence and an angle of reflection at the angle of 60° according to JIS K-5400-1991 7.6.

(c) Erichsen (mm): A steel ball was pushed from the back surface of test piece according to JIS K-5400-1991 8.2.1. to deform the test piece. There was compared the moved length of the ball where cracks or peeling are caused in the coating layer.

(d) Pencil hardness: Scratch test with pencil was according to JIS K-5400-1991 8.4.2. Results were visually evaluated.

(e) Impact strength (cm): In a circumstance at 25° C., a punched piece having the diameter of ½ inch phi was employed at the conditions in which the coated surface was faced upwardly and a weight having 1kg was dropped from various height.

Results were evaluated by comparing maximum height not fractured.

(f) Anti-strippability: Coating layer was cut at interval of 1 mm×1 mm square according to JIS K-5400-1991 7.6. Successively, a test for peeling was tried thrice by sticking tape to compare anti-strippability.

(g) Solvent resistance: Rubbing test (100 cycles) was carried out with xylene, and conditions of the coating layer were compared by visual observation
(○: good, Δ: slightly poor, X: poor).

(h) Weatherability (retention ratio % of 60° Gloss): There was compared retention ratio of 60° C. Gloss after irradiated for 2000 hours with a Sunshine Weather-O-Meter.

In the powder coating composition of the present invention, kneading can be sufficiently carried out by mixing the methacrylic resins prepared using the epoxy(meth) acrylates represented by general formula (1-2) having the epoxy groups having a mild reactivity with carboxylic group.

Furthermore, a melt viscosity of coating layer in baking is moderate.

Still further, in the case when a carboxyl-terminated polyester resin is employed as a curing agent, compatibility between the methacrylic resin and the polyester resin is exceedingly excellent, resulting in being capable of providing coating layers having excellent properties.

While the invention has been described in detail and with reference to specific embodiments thereof, it will be apparent to one skilled in the art that various changes and modifications can be made therein without departing from the spirit and scope thereof.

What is claimed is:

1. An epoxy(meth)acrylate represented by the formula (1-2)

$$CH_2=CR^1-COOCR^{a'}R^{b'}R^{c'} \quad (1-2)$$

wherein $R^1$ is a hydrogen or a methyl group, $R^{a'}$, $R^{b'}$, and $R^{c'}$ are each independently a hydrogen or a substituted group represented by general formula (2-2)

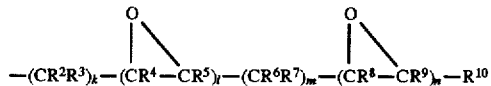

at least one of $R^{a'}$, $R^{b'}$, and $R^{c'}$ is not hydrogen, $R^2$, $R^6$, $R^7$, and $R^{10}$ are each independently hydrogen or an alkyl group having a carbon number of 1 to 10, $R^3$ is independently hydrogen, or an alkyl, alkenyl or epoxy group having a carbon number of 1 to 10, $R^4$, $R^5$, R8 and $R^9$ are each independently hydrogen or an alkyl group having a carbon number of 1 to 5, k is an integer of 0 to 30, l is an integer of 0 to 5, m is an integer of 0 to 30, and n is an integer of 1 to 5 wherein the compound of formula (1-2) contains at least two epoxy groups.

2. An epoxy(meth)acrylate according to claim 1, wherein k is 0, l is 0, m is 6, said $R^6$, $R^7$, $R^8$, $R^9$, and $R^{10}$ are each a hydrogen, and n is 1.

3. An epoxy(meth)acrylate according to claim 1, wherein k is 0, l is 0, m is 2, said $R^6$, R7, $R^9$, and $R^{10}$ are each a hydrogen, said $R^8$ is a methyl group, and n is 1.

4. An epoxy(meth)acrylate according to claim 1, wherein k is 0, l is 0, m is 1, said $R^6$, $R^7$, and $R^8$ are each a hydrogen, and said $R^9$ and $R^{10}$ are each a methyl group, and n is 1.

5. An epoxy(meth)acrylate according to claim 1, wherein k is 1, l is 1, m is 3, said $R^2$, $R^3$, $R^4$, $R^5$, $R^6$, $R^7$, $R^8$, $R^9$, and $R^{10}$ are each a hydrogen, and n is 1.

6. An epoxy(meth)acrylate according to claim 1, wherein k is 1, l is 0, m is 3, $R^3$ is an epoxy group, said $R^2$, $R^6$, $R^7$, $R^8$, $R^9$, and $R^{10}$ are each a hydrogen, and n is 1.

7. A process for the preparation of an epoxy(meth)acrylate of claim 1 which comprises epoxidizing a (meth)acrylate of the formula (1-1)

$$CH_2=CR^1-COOCR^aR^bR^c \quad (1-1)$$

wherein $R^1$ is a hydrogen or a methyl group, $R^a$, $R^b$, and $R^c$ are each independently a hydrogen or a substituted group represented by general formula (2-1)

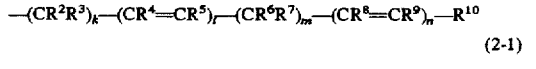

at least one of $R^a$, $R^b$, and $R^c$ is not hydrogen, $R^2$, $R^6$, $R^7$, and $R^{10}$ are each independently hydrogen or an alkyl group having a carbon number of 1 to 10, $R^3$ is independently hydrogen, or an alkyl, alkenyl or epoxy group having a carbon number of 1 to 10, $R^4$, $R^5$, R8 and $R^9$ are each independently hydrogen or an alkyl group having a carbon number of 1 to 5, k is an integer of 0 to 30, l is an integer of 0 to 5, m is an integer of 0 to 30, and n is an integer of 1 to 5.

* * * * *

UNITED STATES PATENT AND TRADEMARK OFFICE
CERTIFICATE OF CORRECTION

PATENT NO. : 5,756,777
DATED : May 26, 1998
INVENTOR(S) : Shinohara et al

It is certified that error appears in the above-indentified patent and that said Letters Patent is hereby corrected as shown below:

Col. 54, line 2, claim 3, "R7" should be --$R^7$--.
Col. 55, line 3, claim 7, "R8" should be --$R^8$--.

Signed and Sealed this

Eighteenth Day of August, 1998

Attest:

BRUCE LEHMAN

Attesting Officer

Commissioner of Patents and Trademarks